(12) United States Patent
Maynard et al.

(10) Patent No.: US 7,282,498 B2
(45) Date of Patent: Oct. 16, 2007

(54) SUBSTITUTED FUSED PYRROLEOXIMES AND FUSED PYRAZOLEOXIMES

(75) Inventors: George Maynard, Clinton, CT (US); LingHong Xie, Guilford, CT (US); Stanislaw Rachwal, Branford, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 10/858,496

(22) Filed: Jun. 1, 2004

(65) Prior Publication Data

US 2005/0059826 A1    Mar. 17, 2005

Related U.S. Application Data

(63) Continuation of application No. 09/947,710, filed on Sep. 6, 2001, now Pat. No. 6,743,817.

(60) Provisional application No. 60/230,498, filed on Sep. 6, 2000.

(51) Int. Cl.
| | |
|---|---|
| *C07D 413/12* | (2006.01) |
| *C07D 403/12* | (2006.01) |
| *C07D 231/54* | (2006.01) |
| *A61K 31/416* | (2006.01) |
| *A61K 31/5377* | (2006.01) |

(52) U.S. Cl. .............. 514/234.5; 514/252.06; 514/338; 514/406; 544/140; 544/238; 546/275.7; 548/360.1

(58) Field of Classification Search .............. 548/360.1
See application file for complete search history.

(56) References Cited

U.S. PATENT DOCUMENTS 5,936,095 A * 8/1999 DeSimone et al. .......... 548/222
6,743,817 B2 * 6/2004 Maynard et al. ............ 514/414

OTHER PUBLICATIONS

Michels et al., "GABAA Receptors: Properties and Trafficking," Crit. Rev. Biochem. Mol. Biol., 42(1), Mar. 14, 2007.*

* cited by examiner

*Primary Examiner*—Golam M. M. Shameem
(74) *Attorney, Agent, or Firm*—McDonnell Boehnen Hulbert & Berghoff LLP

(57) ABSTRACT

Disclosed are compounds of the formula

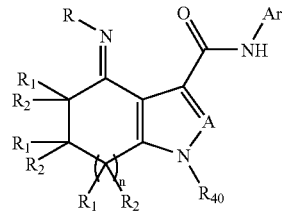

and the pharmaceutically acceptable salts thereof wherein R, Ar, A, n, $R_1$ and $R_2$ are defined herein. These compounds are highly selective agonists, antagonists or inverse agonists for $GABA_A$ brain receptors or prodrugs of agonists, antagonists or inverse agonists for $GABA_A$ brain receptors and are therefore useful in the diagnosis and treatment of anxiety, depression, Down Syndrome, sleep and seizure disorders, overdose with benzodiazepine drugs and for enhancement of memory. Pharmaceutical compositions, including packaged pharmaceutical compositions, are also disclosed.

21 Claims, No Drawings

US 7,282,498 B2

SUBSTITUTED FUSED PYRROLEOXIMES AND FUSED PYRAZOLEOXIMES

This application claims priority from U.S. Provisional Application Ser. No. 60/230,498, filed Sep. 6, 2000, which is hereby incorporated by reference in its entirety.

BACKGROUND OF THE INVENTION

1. Field of the Invention

This invention relates to novel fused pyrroleoximes and fused pyrazoleoximes and other such compounds, and more specifically to preferred fused pyrroleoximes and fused pyrazoleoximes that bind with high selectivity and high affinity to the benzodiazepine site of $GABA_A$ receptors. This invention also relates to pharmaceutical compositions comprising such compounds and to the use of such compounds in treatment of central nervous system (CNS) diseases.

2. Description of the Related Art

The $GABA_A$ receptor superfamily represents one of the classes of receptors through which the major inhibitory neurotransmitter, γ-aminobutyric acid, or GABA, acts. Widely, although unequally, distributed through the mammalian brain, GABA mediates many of its actions through a complex of proteins called the $GABA_A$ receptor, which causes alteration in chloride conductance and membrane polarization.

A number of cDNAs for $GABA_A$ receptor subunits have been characterized. To date at least 6α, 3β, 3γ, 1ε, 1δ and 2ρ subunits have been identified. It is generally accepted that native $GABA_A$ receptors are typically composed of 2α, 2β, and 1γ subunits (Pritchett & Seeburg Science 1989; 245: 1389-1392 and Knight et. al., Recept. Channels 1998; 6:1-18). Evidence such as message distribution, genome localization and biochemical study results suggest that the major naturally occurring receptor combinations are $α_1β_2γ_2$, $α_2β_3γ_2$, $α_3β_3γ_2$, and $α_5β_3γ_2$ (Mohler et. al., Neuroch. Res. 1995; 20(5): 631-636).

Benzodiazepines exert their pharmacological actions by interacting with the benzodiazepine binding sites associated with the $GABA_A$ receptor. In addition to the benzodiazepine site, the $GABA_A$ receptor contains sites of interaction for several other classes of drugs. These include a steroid binding site, a picrotoxin site, and the barbiturate site. The benzodiazepine site of the $GABA_A$ receptor is a distinct site on the receptor complex that does not overlap with the site of interaction for GABA or for other classes of drugs that bind to the receptor (see, e.g., Cooper, et al., The Biochemical Basis of Neuropharmacology, 6th ed., 1991, pp. 145-148, Oxford University Press, New York). Early electrophysiological studies indicated that a major action of the benzodiazepines was enhancement of GABAergic inhibition. Compounds that selectively bind to the benzodiazepine site and enhance the ability of GABA to open $GABA_A$ receptor channels are agonists of GABA receptors. Other compounds that interact with the same site but negatively modulate the action of GABA are called inverse agonists. Compounds belonging to a third class bind selectively to the benzodiazepine site and yet have little or no effect on GABA activity, but can block the action of $GABA_A$ receptor agonists or inverse agonists that act at this site. These compounds are referred to as antagonists.

The important allosteric modulatory effects of drugs acting at the benzodiazepine site were recognized early and the distribution of activities at different receptor subtypes has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have a long history of pharmaceutical use as anxiolytics, these compounds often exhibit a number of unwanted side effects. These may include cognitive impairment, sedation, ataxia, potentiation of ethanol effects, and a tendency for tolerance and drug dependence.

$GABA_A$ selective ligands may also act to potentiate the effects of other CNS active compounds. For example, there is evidence that selective serotonin reuptake inhibitors (SSRIs) may show greater antidepressant activity when used in combination with $GABA_A$ selective ligands than when used alone.

SUMMARY OF THE INVENTION

This invention provides fused pyrroleoximes and pyrazoleoximes that bind, preferably with both high affinity and high selectivity, to the benzodiazepine site of the $GABA_A$ receptor, including human $GABA_A$ receptors.

Thus, the invention provides compounds of Formula I, and pharmaceutical compositions comprising compounds of Formula I.

The invention further comprises methods of treating patients suffering from CNS disorders with an effective amount of a compound of the invention. The patient may be a human or other mammal. Treatment of humans, domesticated companion animals (pet) or livestock animals suffering from CNS disorders with an effective amount of a compound of the invention is encompassed by the invention.

In a separate aspect, the invention provides a method of potentiating the actions of other CNS active compounds. This method comprises administering an effective amount of a compound of the invention with another CNS active compound.

Additionally this invention relates to the use of the compounds of the invention as probes for the localization of $GABA_A$ receptors in tissue sections.

Accordingly, a broad aspect of the invention is directed to compounds of Formula I

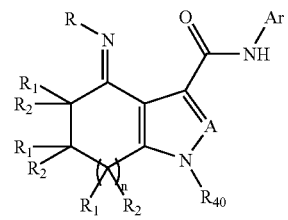

and the pharmaceutically acceptable salts thereof, wherein:

R is hydroxy, hydrocarbyl or —O-hydrocarbyl, where each hydrocarbyl is optionally substituted with oxo, haloalkyl, haloalkoxy, halogen, cyano, hydroxy, alkyl, nitro, azido, alkanoyl, carboxamido, alkoxy, aryloxy, alkylthio, alkylsulfinyl, alkylsulfonyl, amino, mono or dialkylamino, aryl, arylalkyl, arylalkoxy, heteroaryl or heterocycloalkyl; or R is —O-aryl, aryl, —O-heteroaryl, or heteroaryl, each of which is optionally substituted with halogen, cyano, hydroxyl, nitro, azido, alkanoyl, carboxamido, hydrocarbyl, —O-hydrocarbyl, aryloxy, haloalkyl, haloalkoxy, hydrocarbylthio, hydrocarbylsulfinyl, hydrocarbylsulfonyl, amino, mono or dihydrocarbylamino, aryl, arylhydrocarbyl, arylalkoxy, heteroaryl or heterocycloalkyl;

wherein each hydrocarbyl is optionally substituted with 1, 2, 3, 4, or 5 substituents independently selected from the group consisting of oxo, halogen, cyano, nitro, haloalkyl, haloalkoxy, hydroxy, amino, alkyl substituted with 0-2 $R_A$, alkoxy substituted with 0-2 $R_A$, —NH(alkyl) substituted with 0-2 $R_A$, —N(alkyl)(alkyl) where each alkyl is independently substituted with 0-2 $R_A$, phenyl substituted with 0-3 $R_A$, —$XR_B$, and $R_C$; wherein $R_A$ is independently selected at each occurrence from the group consisting of halogen, hydroxy, alkyl, alkoxy, —NH(alkyl), —N(alkyl)(alkyl), heterocycloalkyl, —S(O)$_m$(alkyl), where m is 0, 1, or 2, haloalkyl, haloalkoxy, —CO(alkyl), —CONH(alkyl), —CON(alkyl)(alkyl), —$XR_B$, and Y;

X is independently selected at each occurrence from the group consisting of —CH$_2$—, —CHR$_C$—, —O—, —S(O)$_g$—, —NH—, —NR$_C$—, —C(=O)—, —C(=O)O—, —C(=O)NH—, —C(=O)NR$_C$—, —S(O)$_g$NH—, —S(O)$_g$NR$_C$—, NHC(=O)—, —NR$_C$C(=O)—, —NHS(O)$_g$—, and —NR$_C$S(O)$_g$—; where g is 0, 1, or 2;

$R_B$ and $R_C$ are independently hydrocarbyl which may be further substituted with one or more substituents independently selected from oxo, hydroxy, halogen, amino, —NH(alkyl), —N(alkyl)(alkyl), cyano, nitro, haloalkyl, haloalkoxy, —O(alkyl), —NHC(O)(alkyl), —N(alkyl)C(O)(alkyl), —NHS(O)$_m$(alkyl), —S(O)$_m$(alkyl) —S(O)$_m$NH(alkyl), and —S(O)$_m$N(alkyl)(alkyl); where each m is 0, 1, or 2;

Y is independently selected at each occurrence from 5- to 8-membered carbocycles or heterocycles, which are saturated, partially unsaturated, or aromatic and contain zero, one or two hetero atoms selected from N, O, and S, and which may be further substituted with one or more substituents independently selected from the group consisting of halogen, oxo, hydroxy, amino, mono- or di($C_1$-$C_6$)alkylamino, nitro, cyano, $C_1$-$C_6$ alkyl, $C_1$-$C_6$ alkoxy, and —SO$_a$(alkyl); where a is 0, 1, or 2;

$R_1$ and $R_2$ are independently selected at each occurrence from hydrogen, halogen, hydroxy, hydrocarbyl, —O-hydrocarbyl, alkoxy, haloalkyl, haloalkoxy, nitro, cyano, amino, mono or dihydrocarbylamino;

n is 0, 1, or 2;

A is N or CR$_3$, wherein R$_3$ is hydrogen or hydrocarbyl;

Ar is aryl or heteroaryl, each of which is optionally substituted with 1, 2, or 3 substituents independently selected from the group consisting of oxo, haloalkyl, haloalkoxy, halogen, cyano, hydroxy, nitro, azido, alkanoyl, carboxamido, hydrocarbyl substituted with 0-2 $R_A$, —O-hydrocarbyl substituted with 0-2 $R_A$, aryloxy, alkylthio hydrocarbylsulfinyl, hydrocarbylsulfonyl, amino, —NH(hydrocarbyl) substituted with 0-2 $R_A$, —N(hydrocarbyl)(hydrocarbyl) wherein each hydrocarbyl is substituted with 0-2 $R_A$, aryl, arylhydrocarbyl, arylalkoxy, heteroaryl and heterocycloalkyl; and $R_{40}$ is hydrogen, alkyl, arylalkyl or arylalkanoyl.

The invention also provides intermediates and methods of making the compounds of the invention.

DETAILED DESCRIPTION OF THE INVENTION

In a specific aspect, the invention provides compounds of Formula I where A is nitrogen and n is 0. In another specific aspect, the invention provides compounds of Formula I where A is CR$_3$, where R$_3$ is defined above, and n is 0.

In another specific aspect, the invention provides compounds of Formula I where A is nitrogen and n is 1. In yet another specific aspect, the invention provides compounds of Formula I where A is CR$_3$, where R$_3$ is defined above, and n is 1.

In a yet further specific aspect, the invention provides compounds of Formula I where A is nitrogen and n is 2. In yet another specific aspect, the invention provides compounds of Formula I where A is CR$_3$, where R$_3$ is defined above, and n is 2.

More preferably the invention relates to compounds of Formula I and the pharmaceutically acceptable salts thereof, where R is hydroxy, alkyl, cycloalkyl, alkoxy, or cycloalkyloxy each of which is optionally substituted with oxo, haloalkyl, haloalkoxy halogen, cyano, hydroxy, alkyl, nitro, azido, alkanoyl, carboxamido, alkoxy, aryloxy, alkylthio, alkylsulfinyl, alkylsulfonyl, amino, mono or dialkylamino, aryl, arylalkyl, arylalkoxy, heteroaryl or heterocycloalkyl; or R is phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, pyridizinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, or quinoxalinyl, each of which is optionally mono-, di-, or trisubstituted with substituents independently chosen from halogen, cyano, nitro, haloalkyl, haloalkoxy, hydroxy, amino, alkyl substituted with 0-2 $R_A$, alkoxy substituted with 0-2 $R_A$, —NH(alkyl) substituted with 0-2 $R_A$, —N(alkyl)(alkyl) where each alkyl is independently substituted with 0-2 $R_A$, phenyl substituted with 0-3 $R_A$, —$XR_B$, and $R_C$;

Ar is phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidinyl, pyrazinyl, pyridizinyl, benzimidazolyl, naphthyl, indolyl, isoindolyl, benzofuranyl, isobenzofuranyl, benzo[b]thiophenyl, benz[d]isoxazolyl, quinolinyl, isoquinolinyl, cinnolinyl, quinazolinyl, or quinoxalinyl, each of which is optionally mono-, di-, or trisubstituted with substitutents independently chosen from oxo, halogen, cyano, nitro, haloalkyl, haloalkoxy, hydroxy, amino, alkyl substituted with 0-2 $R_A$, alkoxy substituted with 0-2 $R_A$, —NH(alkyl) substituted with 0-2 $R_A$, —N(alkyl)(alkyl) where each alkyl is independently substituted with 0-2 $R_A$, —$XR_B$, and $R_C$;

$R_A$ is independently selected at each occurrence from the group consisting of halogen, hydroxy, alkyl, alkoxy, —NH(alkyl), —N(alkyl)(alkyl), morpholinyl, pyrrolidinyl, piperidinyl, thiomorpholinyl, piperazinyl, —S(O)$_m$(alkyl), where m is 0, 1, or 2, haloalkyl, haloalkoxyoxy, —CO(alkyl), CONH(alkyl), CON(alkyl)(alkyl), —$XR_B$, and Y, where X, Y, $R_A$, $R_B$, and $R_C$ are as defined with respect to Formula I.

Such compounds are referred to hereinafter as compounds of Formula Ia.

Preferred compounds of Formula Ia are those compounds where each alkyl is $C_1$-$C_6$ alkyl and each alkoxy is $C_1$-$C_6$ alkoxy. Such compounds are referred to hereinafter as compounds of Formula Ib.

Preferred compounds of Formula I include those where

Ar is phenyl, pyridyl, pyrimidinyl, pyrazolyl, or pyridizinyl, each of which is unsubstituted or substituted with up to three groups selected from halogen, cyano, nitro, $C_1$-$C_6$haloalkyl, $C_1$-$C_6$haloalkoxy, hydroxy, amino, and $C_1$-$C_6$alkyl substituted with 0-2 $R_A$, $C_1$-$C_6$alkoxy substituted with 0-2 $R_A$, —NH($C_1$-$C_6$alkyl) substituted with 0-2 $R_A$, and —N($C_1$-$C_6$alkyl)($C_1$-$C_6$alkyl) where each alkyl is independently substituted with 0-2 $R_A$, —$XR_B$, and $R_C$;

$R_A$ is independently selected at each occurrence the group consisting of halogen, hydroxy, $C_1$-$C_6$alkyl, $C_1$-$C_6$alkoxy, —NH ($C_1$-$C_6$alkyl), —N($C_1$-$C_6$alkyl)($C_1$-$C_6$alkyl), $C_1$-$C_6$haloalkyl, $C_1$-$C_6$haloalkoxy, —$XR_B$ and Y;

X is independently selected at each occurrence from the group consisting of —$CH_2$—, —$CHR_C$—, —O—, —NH—, —$NR_C$—, and —C(=O)—;

$R_B$ and $R_C$ are independently $C_1$-$C_6$ alkyl, $C_3$-$C_7$cycloalkyl, or $C_3$-$C_7$cycloalkyl($C_1$-$C_6$)alkyl, each of is optionally substituted with one or more substituents independently selected from oxo, hydroxy, halogen, amino, cyano, nitro, $C_1$-$C_6$ haloalkyl, $C_1$-$C_6$ haloalkoxy, $C_1$-$C_6$ alkyl, $C_1$-$C_6$ alkoxy, mono- or di($C_1$-$C_6$)alkylamino, —NHC(O)($C_{1-6}$ alkyl), and —N($C_1$-$C_6$ alkyl)C(O)($C_1$-$C_6$alkyl), where m is 0, 1, or 2; and Y is morpholinyl, homopiperazinyl, piperazinyl, homo piperidinyl, piperidinyl, tetrahydropyridyl, imidazolyl, imidazolinyl, or imidazolidinyl.

More preferred compounds and pharmaceutically acceptable salts of Formula I include those where R is hydroxy, $C_1$-$C_6$alkyl, cycloalkyl, $C_1$-$C_6$alkoxy, or cycloalkyloxy each of which is optionally substituted with oxo, $C_1$-$C_6$haloalkyl, $C_1$-$C_6$haloalkoxy halogen, cyano, hydroxy, $C_1$-$C_6$alkyl, nitro, azido, $C_1$-$C_6$alkanoyl, carboxamido, $C_1$-$C_6$alkoxy, aryloxy, $C_1$-$C_6$alkylthio, $C_1$-$C_6$alkylsulfinyl, $C_1$-$C_6$alkylsulfonyl, amino, mono or di($C_1$-$C_6$)alkylamino, aryl, aryl($C_1$-$C_4$)alkyl, aryl($C_1$-$C_4$) alkoxy, heteroaryl or heterocycloalkyl; or R is phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidyl, pyrazinyl, pyridizinyl, benzimidazolyl, naphthyl, indolyl, isoindolyl, benzofuranyl, isobenzofuranyl, benzo[b]thiophenyl, benz[d] isoxazolyl, quinolinyl, isoquinolinyl, cinnolinyl, quinazolinyl, or quinoxalinyl, each of which is optionally mono-, di-, or trisubstituted with substituents independently chosen from halogen, cyano, nitro, $C_1$-$C_6$haloalkyl, $C_1$-$C_6$haloalkoxy, hydroxy, amino, $C_1$-$C_6$alkyl substituted with 0-2 $R_A$, $C_1$-$C_6$alkoxy substituted with 0-2 $R_A$, —NH($C_1$-$C_6$alkyl) substituted with 0-2 $R_A$, —N($C_1$-$C_6$alkyl) ($C_1$-$C_6$alkyl) where each alkyl is independently substituted with 0-2 $R_A$, phenyl substituted with 0-3 $R_A$, —$XR_B$, and $R_C$;

$R_1$ and $R_2$ are independently selected at each occurrence from hydrogen, halogen, hydroxy, $C_1$-$C_6$ alkyl, $C_1$-$C_6$ alkoxy, $C_1$-$C_6$haloalkyl, $C_1$-$C_6$haloalkoxy, nitro, cyano, amino, mono- or di-($C_1$-$C_6$)alkylamino;

Ar is phenyl, pyrrolyl, furanyl, thienyl, pyrazolyl, imidazolyl, thiazolyl, isothiazolyl, oxazolyl, isoxazolyl, oxadiazolyl, triazolyl, tetrazolyl, pyridyl, pyrimidinyl, pyrazinyl, pyridizinyl, benzimidazolyl, naphthyl, indolyl, isoindolyl, benzofuranyl, isobenzofuranyl, benzo[b] thiophenyl, benz[d]isoxazolyl, quinolinyl, isoquinolinyl, cinnolinyl, quinazolinyl, or quinoxalinyl, each of which is optionally mono-, di-, or trisubstituted with substituents independently chosen from oxo, halogen, cyano, nitro, $C_1$-$C_6$haloalkyl, $C_1$-$C_6$haloalkoxy, hydroxy, amino, $C_1$-$C_6$alkyl substituted with 0-2 $R_A$, $C_1$-$C_6$alkoxy substituted with 0-2 $R_A$, —NH($C_1$-$C_6$alkyl) substituted with 0-2 $R_A$, —N($C_1$-$C_6$alkyl) ($C_1$-$C_6$alkyl) where each $C_1$-$C_6$alkyl is independently substituted with 0-2 $R_A$, —$XR_B$, and $R_C$;

$R_A$ is independently selected at each occurrence from the group consisting of halogen, hydroxy, $C_1$-$C_6$alkyl, $C_1$-$C_6$alkoxy, —NH($C_1$-$C_6$alkyl), —N($C_1$-$C_6$alkyl) ($C_1$-$C_6$alkyl), morpholinyl, pyrrolidinyl, piperidinyl, thiomorpholinyl, piperazinyl, —S(O)$_m$(alkyl), where m is 0, 1, or 2, $C_1$-$C_6$haloalkyl, $C_1$-$C_6$haloalkoxy, —CO ($C_1$-$C_6$alkyl), CONH($C_1$-$C_6$alkyl), CON($C_1$-$C_6$alkyl) ($C_1$-$C_6$alkyl), —$XR_B$, and Y; and $R_B$ and $R_C$ are independently $C_1$-$C_6$hydrocarbyl which may be further substituted with one or more substituents independently selected from oxo, hydroxy, halogen, amino, —NH($C_1$-$C_6$alkyl), —N($C_1$-$C_6$alkyl) ($C_1$-$C_6$alkyl), cyano, nitro, $C_1$-$C_6$haloalkyl, $C_1$-$C_6$haloalkoxy, —O($C_1$-$C_6$alkyl), —NHC(O)($C_1$-$C_6$alkyl), —N($C_1$-$C_6$alkyl)C(O)($C_1$-$C_6$alkyl), —NHS (O)$_m$($C_1$-$C_6$alkyl), —S(O)$_m$($C_1$-$C_6$alkyl), —S(O)$_m$NH ($C_1$-$C_6$alkyl), and —S(O)$_m$N($C_1$-$C_6$alkyl)($C_1$-$C_6$alkyl); where each m is 0, 1, or 2.

Particularly, the invention includes compounds where A is nitrogen, i.e. compounds of Formula II (below)

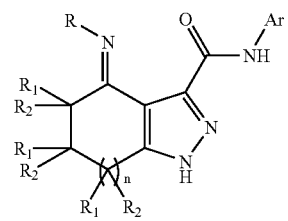

Formula II and the pharmaceutically acceptable salts thereof, wherein n, R, $R_1$, $R_2$, and Ar are as defined for Formula I.

Preferred compounds of Formula II are compounds wherein n is 1 (hereinafter compounds of Formula IIa).

Particularly preferred compounds of Formula IIa are those compounds wherein $R_1$ and $R_2$ are $C_1$-$C_6$ alkyl, $C_1$-$C_6$ alkoxy, hydrogen, cyano, amino, amino($C_1$-$C_6$)alkyl, halo($C_1$-$C_6$)alkyl, or halo($C_1$-$C_6$)alkoxy; and Ar is phenyl, pyridyl, pyrimidinyl, pyrazolyl, or pyridizinyl, each of which is unsubstituted or substituted with up to three groups selected from halogen, cyano, nitro, $C_1$-$C_6$haloalkyl, $C_1$-$C_6$haloalkoxy, hydroxy, amino, and $C_1$-$C_6$alkyl substituted with 0-2 $R_A$, $C_1$-$C_6$alkoxy substituted with 0-2 $R_A$, —NH($C_1$-$C_6$alkyl) substituted with 0-2 $R_A$, and —N($C_1$-$C_6$alkyl)($C_1$-$C_6$alkyl) where each alkyl is independently substituted with 0-2 $R_A$, —$XR_B$, and $R_C$;

$R_A$ is independently selected at each occurrence the group consisting of halogen, hydroxy, $C_1$-$C_6$alkyl, $C_1$-$C_6$alkoxy, —NH($C_1$-$C_6$alkyl), —N($C_1$-$C_6$alkyl) ($C_1$-$C_6$alkyl), $C_1$-$C_6$haloalkyl, $C_1$-$C_6$haloalkoxy, —$XR_B$ and Y;

X is independently selected at each occurrence from the group consisting of —$CH_2$—, —$CHR_C$—, —O—, —NH—, —$NR_C$—, and —C(=O)—;

$R_B$ and $R_C$ are independently $C_1$-$C_6$ alkyl, $C_3$-$C_7$cycloalkyl, or $C_3$-$C_7$cycloalkyl($C_1$-$C_6$)alkyl, each of is optionally substituted with one or more substituents independently selected from oxo, hydroxy, halogen, amino, cyano, nitro, $C_1$-$C_6$ haloalkyl, $C_1$-$C_6$ haloalkoxy, $C_1$-$C_6$ alkyl, $C_1$-$C_6$ alkoxy, mono- or di($C_1$-$C_6$)alkylamino, —NHC(O)($C_{1-6}$ alkyl), and —N($C_1$-$C_6$ alkyl)C(O)($C_1$-$C_6$ alkyl), where m is 0, 1, or 2; and Y is morpholinyl, homopiperazinyl, piperazinyl, homo piperidinyl, piperidinyl, tetrahydropyridyl, imidazolyl, imidazolinyl, or imidazolidinyl.

Such compounds are referred to hereinafter as compounds of Formula IIc. Preferred compounds of Formula IIc are those compounds wherein $R_1$ and $R_2$ are defined as for Formula IIc and R is $C_1$-$C_6$ alkyl or —O—$C_1$-$C_6$alkyl, wherein $C_1$-$C_6$ alkyl is straight or branched and may contain double or triple bonds; or R is $C_3$-$C_7$ cycloalkyl or —O—$C_3$-$C_7$alkyl or R is phenyl or pyridyl, wherein each phenyl or pyridyl is unsubstituted or mono-, di-, or trisubstituted with halogen, cyano, nitro, halo($C_1$-$C_6$)alkyl, halo($C_1$-$C_6$)alkoxy, hydroxy, amino, $C_1$-$C_6$alkyl substituted with 0-2 $R_A$, $C_1$-$C_6$alkoxy substituted with 0-2 $R_A$, —NH($C_{1-6}$ alkyl) substituted with 0-2 $R_A$, —N($C_1$-$C_6$alkyl)($C_1$-$C_6$alkyl) where each $C_1$-$C_6$alkyl is independently substituted with 0-2 $R_A$, phenyl substituted with 0-3 $R_A$, —$XR_B$, and $R_C$, wherein X, $R_A$, $R_B$, and $R_C$ are defined as for Formula I.

Such compounds are referred to hereinafter as compounds of Formula IId. Also preferred are compounds of Formula II, IIa, IIc, and IId wherein $R_1$ and $R_2$ are independently selected at each occurrence from hydrogen, halogen, methyl and ethyl.

As noted above, preferred compounds of Formula II include those where n is 1. Other preferred compounds of Formula II are those where n is 0, or where n is 2.

Other preferred compounds and pharmaceutically acceptable salts of Formula I are those wherein:

Ar is phenyl, pyridyl, or pyridizinyl each of which is optionally mono-, di-, or tri-substituted with substituents independently chosen from halogen, $C_1$-$C_6$ alkyl, $C_1$-$C_6$ alkoxy, amino, mono- or di($C_1$-$C_6$)alkylamino, $C_1$-$C_6$alkoxy ($C_1$-$C_6$)alkoxy, $C_1$-$C_6$ alkylamino($C_1$-$C_6$)alkoxy, amino($C_1$-$C_6$)alkoxy, di($C_1$-$C_6$)alkylamino($C_1$-$C_6$)alkoxy, $C_1$-$C_6$alkoxy($C_1$-$C_6$)alkylamino, alkyl substituted with morpholinyl, homopiperazinyl, piperazinyl, homopiperidinyl, piperidinyl, tetrahydropyridyl, imidazolyl, imidazolinyl, or imidazolidinyl, and $C_1$-$C_6$ alkoxy substituted with morpholinyl, homopiperazinyl, piperazinyl, homo piperidinyl, piperidinyl, tetrahydropyridyl, imidazolyl, imidazolinyl, and imidazolidinyl.

The invention also includes compounds and pharmaceutically acceptable salts of Formula II wherein Ar is phenyl, pyridyl, or pyridinzyl, each of which is substituted with one of i) halogen, $C_1$-$C_6$ alkyl, $C_1$-$C_6$ alkoxy, mono- or di-($C_1$-$C_6$) alkylamino, $C_1$-$C_6$alkoxy($C_1$-$C_6$)alkoxy, mono or di-($C_1$-$C_6$)alkylamino($C_1$-$C_6$)alkoxy, or ii) $C_1$-$C_6$ alkoxy substituted with morpholinyl, homopiperazinyl, piperazinyl, homopiperidinyl, piperidinyl, tetrahydropyridyl, imidazolyl, imidazolinyl, or imidazolidinyl and Ar is optionally further substituted with one or two substitutents independently chosen from halogen, $C_1$-$C_4$ alkyl, $C_1$-$C_4$ alkoxy, amino, $C_1$-$C_6$ alkylamino, $C_1$-$C_3$ alkoxy ($C_1$-$C_3$)alkoxy, $C_1$-$C_3$ alkylamino($C_1$-$C_3$)alkoxy, amino ($C_1$-$C_3$)alkoxy, $C_1$-$C_3$ alkylamino($C_1$-$C_3$)alkoxy, and $C_1$-$C_6$ alkoxy($C_1$-$C_6$)alkylamino.

Particularly preferred definitions for the variables $R_1$ and $R_2$ of Formula II include hydrogen, $C_1$-$C_2$ alkyl, $C_1$-$C_2$ alkoxy, cyano, amino, and halogen. It is also preferred that not more than three of $R_1$ and $R_2$ are other than hydrogen. More preferred compounds and salts of Formula II are those wherein one, two, or three of $R_1$ and $R_2$ are independently chosen from hydrogen, halogen, methyl and ethyl, and the remaining $R_1$ and $R_2$ substituents are hydrogen.

The invention is further directed to compounds and salts of Formula II, wherein

R is $C_1$-$C_6$alkyl, $C_1$-$C_6$alkoxy, phenyl($C_1$-$C_6$)alkyl, pyridyl ($C_1$-$C_6$)alkyl, phenyl or pyridyl, wherein each phenyl or pyridyl is unsubstituted or mono-, di-, or trisubstituted with halogen, cyano, nitro, halo($C_1$-$C_6$)alkyl, halo($C_1$-$C_6$) alkoxy, hydroxy, amino, $C_1$-$C_6$alkyl substituted with 0-2 $R_A$, $C_1$-$C_6$alkoxy substituted with 0-2 $R_A$, —NH($C_{1-6}$ alkyl) substituted with 0-2 $R_A$, —N($C_1$-$C_6$alkyl)($C_1$-$C_6$alkyl) where each $C_1$-$C_6$alkyl is independently substituted with 0-2 $R_A$, phenyl substituted with 0-3 $R_A$, —$XR_B$, and $R_C$.

Furthermore the invention is directed to compounds and pharmaceutically acceptable salts of Formula II wherein R is $C_{1-6}$ alkyl, $C_{1-6}$ alkoxy, or phenyl ($C_1$-$C_6$)alkyl, pyridyl($C_1$-$C_6$)alkyl, phenyl or pyridyl, where the aromatic portion of each is unsubstituted or mono-, di-, or trisubstituted with halogen, cyano, nitro, $C_1$-$C_6$haloalkyl, $C_1$-$C_6$haloalkoxy, hydroxy, amino, $C_1$-$C_6$ alkoxy, or $C_{1-6}$ alkyl.

The invention is also directed to compounds and pharmaceutically acceptable salts of Formula II wherein R is $C_1$-$C_4$alkyl, $C_1$-$C_4$alkoxy, or phenyl, where the phenyl is mono- or di-substituted with substituents independently chosen from halogen, cyano, nitro, $C_1$-$C_6$haloalkyl, $C_1$-$C_6$haloalkoxy, hydroxy, amino, $C_1$-$C_6$ alkoxy, $C_{1-6}$ alkyl, amino($C_1$-$C_6$)alkyl, mono- or di($C_1$-$C_6$)alkylamino ($C_1$-$C_6$)alkyl, and mono- or di($C_1$-$C_6$)alkylamino($C_1$-$C_6$) alkoxy.

Particularly included in the invention are compounds and pharmaceutically acceptable salts of Formula II wherein:

Ar is phenyl, pyridyl, pyrimidinyl, pyrazolyl, or pyridizinyl, each of which is unsubstituted or substituted with up to three groups independently selected from halogen, cyano, nitro, $C_1$-$C_6$haloalkyl, $C_1$-$C_6$haloalkoxy, hydroxy, amino, and $C_1$-$C_6$alkyl substituted with 0-2 $R_A$, $C_1$-$C_6$alkoxy substituted with 0-2 $R_A$, —NH($C_1$-$C_6$alkyl) substituted with 0-2 $R_A$, —N($C_1$-$C_6$alkyl)($C_1$-$C_6$alkyl) where each alkyl is independently substituted with 0-2 $R_A$, —$XR_B$, and $R_C$;

$R_A$ is independently selected at each occurrence the group consisting of halogen, hydroxy, $C_1$-$C_6$alkyl, $C_1$-$C_6$alkoxy, —NH($C_1$-$C_6$alkyl), —N($C_1$-$C_6$alkyl)($C_1$-$C_6$alkyl), $C_1$-$C_6$haloalkyl, $C_1$-$C_6$haloalkoxy, CO($C_1$-$C_6$alkyl), CONH($C_1$-$C_6$alkyl), CON($C_1$-$C_6$alkyl) ($C_1$-$C_6$alkyl), —$XR_B$ and Y;

X is independently selected at each occurrence from the group consisting of —$CH_2$—, —$CHR_C$—, —O—, —S(O)g—, —NH—, —$NR_C$—, —C(=O)—, —C(=O)O—, —C(=O)NH—, —C(=O)$NR_C$—, —S(O)$_g$NH—, —S(O)$_g$$NR_C$—, NHC(=O)—, —$NR_C$C(=O)—, —NHS(O)$_g$—, and —$NR_C$S(O)$_g$—; where g is 0, 1, or 2;

$R_B$ and $R_C$ are independently alkyl groups which may be further substituted with one or more substituent(s) selected from oxo, hydroxy, halogen, amino, cyano, nitro, $C_1$-$C_6$haloalkyl, $C_1$-$C_6$haloalkoxy, —O($C_1$-$C_6$alkyl), —NH($C_{1-6}$ alkyl), —N($C_1$-$C_6$alkyl)($C_{1-6}$ alkyl), —NHC(O)($C_1$-$C_6$alkyl), —N(alkyl)C(O)($C_1$-$C_6$alkyl), —NHS(O)$_m$($C_1$-$C_6$alkyl), —S(O)$_m$($C_1$-$C_6$alkyl), —S(O)$_m$NH($C_1$-$C_6$alkyl), and —S(O)$_m$N($C_1$-$C_6$alkyl)($C_1$-$C_6$alkyl); where m is 0, 1, or 2; and Y is morpholinyl, homopiperazinyl, piperazinyl, homo piperidinyl, piperidinyl, tetrahydropyridyl, imidazolyl, imidazolinyl, or imidazolidinyl, each of which is unsubstituted or further substituted with one or more substituents independently chosen from halogen, oxo, hydroxy, amino, mono- or di($C_1$-$C_6$)alkylamino, nitro, cyano, $C_1$-$C_6$alkyl, $C_1$-$C_6$ alkoxy.

Particularly preferred compounds and pharmaceutically acceptable salts of Formula II are those Where Ar is phenyl, 2-pyridyl, 3-pyridyl or pyridinzyl, each of which is substituted at the position para to the point of attachment of Ar with one of:

i) halogen, $C_1$-$C_6$ alkyl, $C_1$-$C_6$ alkoxy, mono- or di-($C_1$-$C_6$) alkylamino, $C_1$-$C_6$alkoxy($C_1$-$C_6$)alkoxy, mono or di-($C_1$-$C_6$)alkylamino($C_1$-$C_6$)alkoxy, or ii) $C_1$-$C_6$alkoxy substituted with morpholinyl, homopiperazinyl, piperazinyl, homopiperidinyl, piperidinyl, tetrahydropyridyl, imidazolyl, imidazolinyl, or imidazolidinyl; and Ar is optionally further substituted with one or two substituents independently chosen from:

halogen, $C_1$-$C_4$ alkyl, $C_1$-$C_4$ alkoxy, amino, $C_1$-$C_6$ alkylamino, $C_1$-$C_3$ alkoxy($C_1$-$C_3$)alkoxy, $C_1$-$C_3$ alkylamino($C_1$-$C_3$)alkoxy, amino($C_1$-$C_3$)alkoxy, $C_1$-$C_3$ alkylamino($C_1$-$C_3$)alkoxy, and $C_1$-$C_6$ alkoxy ($C_1$-$C_6$) alkylamino;

R is $C_1$-$C_4$ alkoxy; and one, two, or three of $R_1$ and $R_2$ are independently hydrogen, halogen, methyl or ethyl, and the remaining $R_1$ and $R_2$ substituents are hydrogen.

Other particularly preferred compounds and pharmaceutically acceptable salts of Formula II are those wherein Ar is phenyl or 2-pyridyl, each of which is substituted at the position meta to the point of attachment of Ar with one of i) halogen, $C_1$-$C_6$ alkyl, $C_1$-$C_6$ alkoxy, mono- or di-($C_1$-$C_6$) alkylamino, $C_1$-$C_6$alkoxy($C_1$-$C_6$)alkoxy, mono or di-($C_1$-$C_6$)alkylamino($C_1$-$C_6$)alkoxy, or ii) $C_1$-$C_6$alkoxy substituted with morpholinyl, homopiperazinyl, piperazinyl, homopiperidinyl, piperidinyl, tetrahydropyridyl, imidazolyl, imidazolinyl, or imidazolidinyl; and Ar is optionally further substituted with one or two substituents independently chosen from:

halogen, $C_1$-$C_4$ alkyl, $C_1$-$C_4$ alkoxy, amino, $C_1$-$C_6$ alkylamino, $C_1$-$C_3$ alkoxy($C_1$-$C_3$)alkoxy, $C_1$-$C_3$ alkylamino($C_1$-$C_3$)alkoxy, amino($C_1$-$C_3$)alkoxy, $C_1$-$C_3$ alkylamino($C_1$-$C_3$)alkoxy, and $C_1$-$C_6$ alkoxy($C_1$-$C_6$) alkylamino;

R is $C_1$-$C_4$ alkoxy; and one, two, or three of $R_1$ and $R_2$ are independently hydrogen, halogen, methyl or ethyl, and the remaining $R_1$ and $R_2$ substituents are hydrogen.

The invention further includes compounds where A is C—$R_3$, i.e. compounds of Formula III

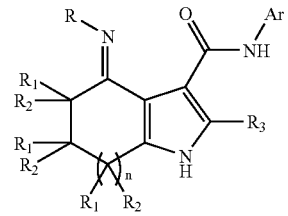

Formula III and the pharmaceutically acceptable salts thereof, wherein n, R, $R_1$, $R_2$, $R_3$, and Ar are as defined for Formula I.

Preferred compounds of Formula III are compounds wherein n is 1 (hereinafter compounds of Formula IIIa).

The invention is particularly directed to compounds and pharmaceutically acceptable salts of Formula III wherein Ar is phenyl, pyridyl, pyrimidinyl, pyrazolyl, or pyridizinyl, each of which is unsubstituted or substituted with up to three groups independently selected from halogen, cyano, nitro, $C_1$-$C_6$haloalkyl, $C_1$-$C_6$haloalkoxy, hydroxy, amino, and $C_1$-$C_6$alkyl substituted with 0-2 $R_A$, $C_1$-$C_6$alkoxy substituted with 0-2 $R_A$, —NH($C_1$-$C_6$alkyl) substituted with 0-2 $R_A$, and —N($C_1$-$C_6$alkyl)($C_1$-$C_6$alkyl) where each alkyl is independently substituted with 0-2 $R_A$, —X$R_B$, and $R_C$;

$R_A$ is independently selected at each occurrence the group consisting of halogen, hydroxy, $C_1$-$C_6$alkyl, $C_1$-$C_6$alkoxy, —NH($C_1$-$C_6$alkyl), —N($C_1$-$C_6$alkyl)($C_1$-$C_6$alkyl) $C_1$-$C_6$haloalkyl, $C_1$-$C_6$haloalkoxy, —X$R_B$ and Y;

X is independently selected at each occurrence from the group consisting of —$CH_2$—, —$CHR_C$—, —O—, —NH—, —$NR_C$—, and —C(=O)—;

$R_B$ and $R_C$ are independently $C_1$-$C_6$ alkyl, $C_3$-$C_7$cycloalkyl, or $C_3$-$C_7$cycloalkyl($C_1$-$C_6$)alkyl, each of is optionally substituted with one or more substituents independently selected from oxo, hydroxy, halogen, amino, cyano, nitro, $C_1$-$C_6$ haloalkyl, $C_1$-$C_6$haloalkoxy, $C_1$-$C_6$ alkyl, $C_1$-$C_6$ alkoxy, mono- or di($C_1$-$C_6$)alkylamino, —NHC(O)($C_1$-$C_6$alkyl), and —N($C_1$-$C_6$alkyl)C(O)($C_1$-$C_6$alkyl), where m is 0, 1, or 2; and Y is morpholinyl, homopiperazinyl, piperazinyl, homo piperidinyl, piperidinyl, tetrahydropyridyl, imidazolyl, imidazolinyl, or imidazolidinyl.

More preferably Ar in Formula III is phenyl, pyridyl, or pyridizinyl each of which is optionally mono-, di-, or tri-substituted with substituents independently chosen from halogen, $C_1$-$C_6$ alkyl, $C_1$-$C_6$ alkoxy, amino, mono- or di($C_1$-$C_6$)alkylamino, $C_1$-$C_6$alkoxy($C_1$-$C_6$)alkoxy, $C_1$-$C_6$ alkylamino($C_1$-$C_6$)alkoxy, amino($C_1$-$C_6$)alkoxy, di($C_1$-$C_6$)alkylamino($C_1$-$C_6$)alkoxy, $C_1$-$C_6$ alkoxy($C_1$-$C_6$)alkylamino, alkyl substituted with morpholinyl, homopiperazinyl, piperazinyl, homopiperidinyl, piperidinyl, tetrahydropyridyl, imidazolyl, imidazolinyl, or imidazolidinyl, or $C_1$-$C_6$ alkoxy substituted with morpholinyl, homopiperazinyl, piperazinyl, homopiperidinyl, piperidinyl, tetrahydropyridyl, imidazolyl, imidazolinyl, or imidazolidinyl.

The invention is also directed to compounds of Formula III in which R, $R_1$, $R_2$, $R_3$ and n are as defined for Formula III and Ar is phenyl, pyridyl, or pyridinzyl, each of which is substituted with one of i) halogen, $C_1$-$C_6$ alkyl, $C_1$-$C_6$ alkoxy, mono- or di-($C_1$-$C_6$) alkylamino, $C_1$-$C_6$alkoxy($C_1$-$C_6$)alkoxy, mono or di-($C_1$-$C_6$)alkylamino($C_1$-$C_6$)alkoxy, or ii) $C_1$-$C_6$ alkoxy substituted with morpholinyl, homopiperazinyl, piperazinyl, homopiperidinyl, piperidinyl, tetrahydropyridyl, imidazolyl, imidazolinyl, or imidazolidinyl and Ar is optionally further substituted with one or two substituents independently chosen from:
halogen, $C_1$-$C_4$ alkyl, $C_1$-$C_4$ alkoxy, amino, $C_1$-$C_6$ alkylamino, $C_1$-$C_3$ alkoxy($C_1$-$C_3$)alkoxy, $C_1$-$C_3$ alkylamino($C_1$-$C_3$)alkoxy, amino($C_1$-$C_3$)alkoxy, $C_1$-$C_3$ alkylamino($C_1$-$C_3$)alkoxy, and $C_1$-$C_6$alkoxy($C_1$-$C_6$)alkylamino.

Such compounds are referred to hereinafter as compounds of Formula IIIb.

Particularly preferred definitions for the variables $R_1$ and $R_2$ of Formula III include hydrogen, $C_1$-$C_2$ alkyl, $C_1$-$C_2$ alkoxy, cyano, amino, and halogen. It is also preferred that not more than three of $R_1$ and $R_2$ are other than hydrogen. More preferred compounds and salts of Formula III are those wherein one, two, or three of $R_1$ and $R_2$ are independently chosen from hydrogen, halogen, methyl and ethyl, and the remaining $R_1$ and $R_2$ substituents are hydrogen.

Other preferred compounds and pharmaceutically acceptable salts of the invention are those wherein Ar is as defined for compounds of Formula IIIb;

n and $R_3$ are as defined for Formula III;

R is $C_1$-$C_6$alkyl, $C_1$-$C_6$alkoxy, phenyl($C_1$-$C_6$)alkyl, pyridyl($C_1$-$C_6$)alkyl, phenyl or pyridyl, wherein each phenyl or pyridyl is unsubstituted or mono-, di-, or tri-substituted with halogen, cyano, nitro, halo($C_1$-$C_6$)alkyl, halo($C_1$-$C_6$)alkoxy, hydroxy, amino, $C_1$-$C_6$alkyl substituted with 0-2 $R_A$, $C_1$-$C_6$alkoxy substituted with 0-2 $R_A$, —NH($C_{1-6}$alkyl) substituted with 0-2 $R_A$, —N($C_1$-$C_6$alkyl)($C_1$-$C_6$alkyl) where each $C_1$-$C_6$alkyl is independently substituted with 0-2 $R_A$, phenyl substituted with 0-3 $R_A$, —$XR_B$, and $R_C$ (X, $R_B$, and $R_C$ are defined as for Formula III) and one, two, or three of $R_1$ and $R_2$ are independently chosen from hydrogen, halogen, methyl and ethyl, and the remaining $R_1$ and $R_2$ substituents are hydrogen.

Such compounds are referred to as compounds of Formula IIIc.

Particularly preferred compounds and salts of Formula IIIc are those wherein

R is $C_{1-6}$ alkyl, $C_{1-6}$ alkoxy, or
phenyl($C_1$-$C_6$)alkyl, pyridyl($C_1$-$C_6$)alkyl, phenyl or pyridyl, wherein each phenyl or pyridyl is unsubstituted or mono-, di-, or trisubstituted with substituents independently chosen from halogen, cyano, nitro, $C_1$-$C_6$haloalkyl, $C_1$-$C_6$haloalkoxy, hydroxy, amino, $C_1$-$C_6$ alkoxy, and $C_{1-6}$ alkyl.

Other preferred compounds and pharmaceutically acceptable salts of Formula III are those wherein Ar is phenyl, pyridyl, pyrimidinyl, pyrazolyl, or pyridizinyl, each of which is unsubstituted or substituted with up to three groups independently selected from:
halogen, cyano, nitro, $C_1$-$C_6$haloalkyl, $C_1$-$C_6$haloalkoxy, hydroxy, amino, and $C_1$-$C_6$alkyl substituted with 0-2 $R_A$, $C_1$-$C_6$alkoxy substituted with 0-2 $R_A$, —NH($C_1$-$C_6$alkyl) substituted with 0-2 $R_A$, —N($C_1$-$C_6$alkyl)($C_1$-$C_6$alkyl) where each alkyl is independently substituted with 0-2 $R_A$, —$XR_B$, and $R_C$;

$R_A$ is independently selected at each occurrence the group consisting of halogen, hydroxy, $C_1$-$C_6$alkyl, $C_1$-$C_6$alkoxy, —NH($C_1$-$C_6$alkyl), —N($C_1$-$C_6$alkyl)($C_1$-$C_6$alkyl), $C_1$-$C_6$haloalkyl, $C_1$-$C_6$haloalkoxy, CO($C_1$-$C_6$alkyl), CONH($C_1$-$C_6$alkyl), CON($C_1$-$C_6$alkyl)($C_1$-$C_6$alkyl), —$XR_B$ and Y;

X is independently selected at each occurrence from the group consisting of —$CH_2$—, —$CHR_C$—, —O—, —$S(O)_g$—, —NH—, —$NR_C$—, —C(=O)—, —C(=O)O—, —C(=O)NH—, —C(=O)$NR_C$—, —$S(O)_g$NH—, —$S(O)_g$$NR_C$—, NHC(=O)—, —$NR_C$C(=O)—, —NHS(O)$_n$—, and —$NR_C$S(O)$_n$—; where g is 0, 1, or 2;

$R_B$ and $R_C$ are independently alkyl groups which may be further substituted with one or more substituent(s) selected from oxo, hydroxy, halogen, amino, cyano, nitro, $C_1$-$C_6$haloalkyl, $C_1$-$C_6$haloalkoxy, —O($C_1$-$C_6$alkyl), —NH($C_{1-6}$alkyl), —N($C_1$-$C_6$alkyl)($C_{1-6}$alkyl), —NHC(O)($C_1$-$C_6$alkyl), —N(alkyl)C(O)($C_1$-$C_6$alkyl), —NHS(O)$_m$($C_1$-$C_6$alkyl), —S(O)$_m$($C_1$-$C_6$alkyl), —S(O)$_m$NH($C_1$-$C_6$alkyl), and —S(O)$_m$N($C_1$-$C_6$alkyl)($C_1$-$C_6$alkyl); where m is 0, 1, or 2; and Y is morpholinyl, homopiperazinyl, piperazinyl, homopiperidinyl, piperidinyl, tetrahydropyridyl, imidazolyl, imidazolinyl, or imidazolidinyl, each of which is unsubstituted or further substituted with one or more substituents independently chosen from halogen, oxo, hydroxy, amino, mono- or di($C_1$-$C_6$)alkylamino, nitro, cyano, $C_1$-$C_6$alkyl, $C_1$-$C_6$ alkoxy.

Such compounds are referred to hereinafter as compounds of Formula IIId.

Preferred compounds and pharmaceutically acceptable salts of Formula IIId are those wherein R is $C_1$-$C_4$alkyl, $C_1$-$C_4$alkoxy, or phenyl, where the phenyl is mono- or di-substituted with substituents independently chosen from halogen, cyano, nitro, $C_1$-$C_6$haloalkyl, $C_1$-$C_6$haloalkoxy, hydroxy, amino, $C_1$-$C_6$ alkoxy, $C_{1-6}$ alkyl, amino($C_1$-$C_6$)alkyl, mono- or di($C_1$-$C_6$)alkylamino($C_1$-$C_6$)alkyl, and mono- or di($C_1$-$C_6$)alkylamino($C_1$-$C_6$)alkoxy.

The invention specifically embraces compounds of Formulae IV, V, VI, VII, VIII, and IX.

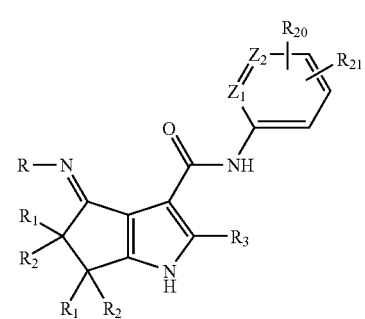

IV

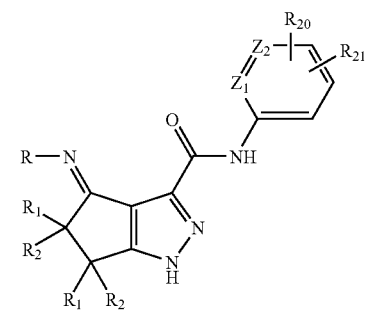

V

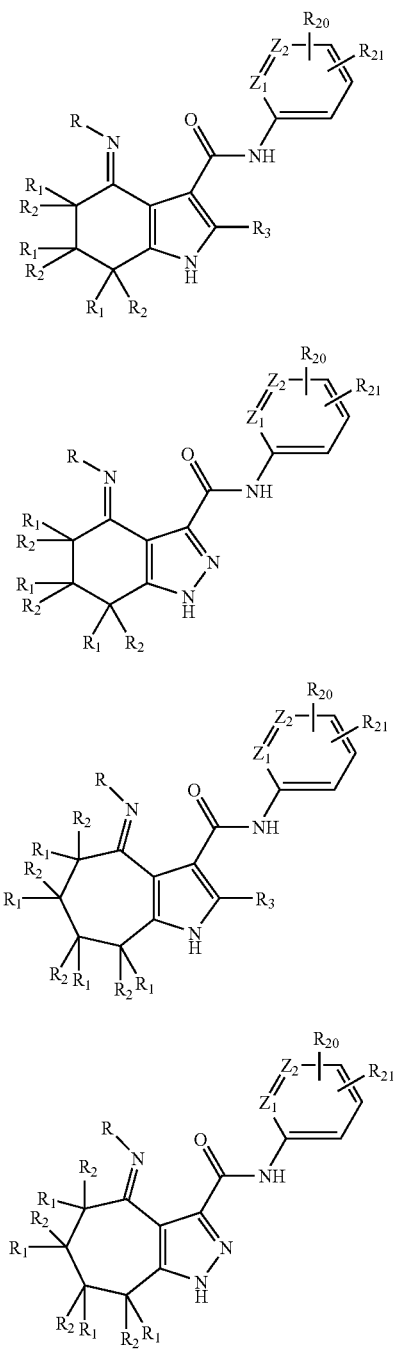

In each of Formulae IV-IX, $Z_1$ and $Z_2$ are independently CH or nitrogen, each R, $R_1$ and $R_2$ independently carries the same definition assigned with respect to Formula I, and $R_{20}$ and $R_{21}$ are independently hydrogen, halogen, $C_1$-$C_6$ alkyl, $C_1$-$C_6$ alkoxy, amino, mono- or di($C_1$-$C_6$)alkylamino, $C_1$-$C_6$ alkoxy($C_1$-$C_6$)alkoxy, $C_1$-$C_6$ alkylamino($C_1$-$C_6$)alkoxy, amino($C_1$-$C_6$)alkoxy, di($C_1$-$C_6$)alkylamino($C_1$-$C_6$)alkoxy, $C_1$-$C_6$ alkoxy($C_1$-$C_6$)alkylamino, or ($C_5$-$C_7$)heterocycloalkyl($C_1$-$C_6$)alkoxy. Preferred heterocycloalkyl groups in Formulae IV-IX are morpholinyl, piperidinyl, and piperazinyl.

Preferably one of $R_{20}$ and $R_{21}$ is hydrogen, $C_1$-$C_2$ alkyl, halogen, or $C_1$-$C_2$alkoxy and the other is morpholinyl- or piperidinyl-($C_2$-$C_4$)alkoxy, or mono- or di($C_1$-$C_3$)alkylamino($C_2$-$C_4$) alkoxy. More preferably, one of $R_{20}$ and $R_{21}$ is hydrogen or halogen and the other is mono- or di($C_1$-$C_3$) alkylamino($C_2$-$C_3$)alkoxy or morpholinyl- or piperidinyl-($C_2$-$C_4$)alkoxy.

Preferred R groups in Formulae IV to IX include hydroxy and $C_1$-$C_3$ alkoxy. More preferred R groups are methoxy and ethoxy.

Particularly preferred compounds of Formulae IV to IX are those where one of $R_{20}$ and $R_{21}$ is hydrogen or halogen in the 2- or 3-position with respect to the point of attachment of the 6-membered aromatic ring to the amide nitrogen and the other is in the 3- or, more preferably, in the 4-position with respect to the point of attachment to the amide nitrogen.

In Formulae IV to IX, preferably one of $Z_1$ and $Z_2$ is CH and the other is CH or both of $Z_1$ and $Z_2$ are CH. More preferred compounds of IV to IX are those where both $Z_1$ and $Z_2$ are CH.

Preferably, $R_1$ and $R_2$ are independently selected at each occurrence from hydrogen, halogen, hydroxy, $C_{1-6}$alkyl, $C_{1-6}$ alkoxy, trifluoromethyl, trifluoromethoxy, nitro, cyano, amino, mono- or di($C_{1-6}$)alkylamino. More preferably, $R_1$ and $R_2$ are independently selected at each occurrence from hydrogen, methyl and ethyl.

Preferred R groups in Formulae IV-IX are R is $C_{1-6}$ alkyl, $C_{1-6}$ alkoxy, or phenyl($C_1$-$C_6$)alkyl, pyridyl($C_1$-$C_6$)alkyl, phenyl or pyridyl,
where the aromatic portion of each is unsubstituted or mono-, di-, or trisubstituted with halogen, cyano, nitro, trifluoromethyl, trifluoromethoxy, hydroxy, amino, $C_1$-$C_6$ alkoxy, or $C_{1-6}$ alkyl.

This invention provides fused pyrroleoxime and pyrazoleoxime derivatives. Preferred examples of the invention bind with high affinity to the benzodiazepine site of $GABA_A$ receptors, including human $GABA_A$ receptors. Particularly preferred compounds are those that bind with high selectivity to the benzodiazepine site of $GABA_A$ receptors, including human $GABA_A$ receptors. Without wishing to be bound to any particular theory, it is believed that the interaction of the compounds of Formula I with the benzodiazepine site results in the pharmaceutical utility of these compounds.

The invention further comprises methods of treating patients in need of such treatment with an amount of a compound of the invention sufficient to alter the symptoms of a CNS disorder. Compounds of the inventions that act as agonists at $\alpha_2\beta_3\gamma_2$ and $\alpha_3\beta_3\gamma_2$ receptor subtypes are useful in treating anxiety disorders such as panic disorder, obsessive compulsive disorder and generalized anxiety disorder; stress disorders including post-traumatic stress, and acute stress disorders. Compounds of the inventions that act as agonists at $\alpha_2\beta_3\gamma_2$ and $\alpha_3\beta_3\gamma_2$ receptor subtypes are also useful in treating depressive or bipolar disorders and in treating sleep disorders. Compounds of the invention that act as inverse agonists at the $\alpha_5\beta_3\gamma_2$ receptor subtype or $\alpha_1\beta_2\gamma_2$ and $\alpha_5\beta_3\gamma_2$ receptor subtypes are useful in treating cognitive disorders including those resulting from Down Syndrome, neurodegenerative diseases such as Alzheimer's disease and Parkinson's disease, and stroke related dementia. Compounds of the invention that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

The diseases and/or disorders that can also be treated using compounds and compositions according to the invention include:

Depression, e.g. depression, atypical depression, bipolar disorder, depressed phase of bipolar disorder.

Anxiety, e.g. general anxiety disorder (GAD), agoraphobia, panic disorder +/−agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g. sleep disorders including primary insomnia, circadian rhythm sleep disorder, dipssomania NOS, parasomnias, including nightmare disorder, sleep terror disorder, sleep disorders secondary to depression and/or anxiety or other mental disorders, substance induced sleep disorder.

Cognition Impairment, e.g. cognition impairment, Alzheimer's disease, Parkinson's disease, mild cognitive impairment (MCI), age-related cognitive decline (ARCD), stroke, traumatic brain injury, AIDS associated dementia, and dementia associated with depression, anxiety or psychosis.

Attention Deficit Disorder, e.g. attention deficit disorder (ADD), and attention deficit and hyperactivity disorder (ADHD).

The invention also provides pharmaceutical compositions comprising compounds of the invention, including packaged pharmaceutical compositions for treating disorders responsive to $GABA_A$ receptor modulation, e.g., treatment of anxiety, depression, sleep disorders or cognitive impairment by $GABA_A$ receptor modulation. The packaged pharmaceutical compositions include a container holding a therapeutically effective amount of at least one $GABA_A$ receptor modulator as described supra and instructions (e.g., labeling) indicating the contained $GABA_A$ receptor ligand is to be used for treating a disorder responsive to $GABA_A$ receptor modulation in the patient.

In a separate aspect, the invention provides a method of potentiating the actions of other CNS active compounds, which comprises administering an effective amount of a compound of the invention in combination with another CNS active compound. Such CNS active compounds include, but are not limited to the following: for anxiety, serotonin receptor (e.g. $5\text{-}HT_{1A}$) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Particularly the invention provides a method of potentiating the antidepressant activity of selective serotonin reuptake inhibitors (SSRIs) by administering an effective amount of a GABA agonist compound of the invention in combination with an SSRI.

Combination administration can be carried out in a fashion analogous to that disclosed in Da-Rocha, et al., *J. Psychopharmacology* (1997) 11(3) 211-218; Smith, et al., *Am. J. Psychiatry* (1998) 155(10) 1339-45; or Le, et al., *Alcohol and Alcoholism* (1996) 31 Suppl. 127-132. Also see, the discussion of the use of the $GABA_A$ receptor ligand 3-(5-methylisoxazol-3-yl)-6-(1-methyl-1,2,3-triazol-4-yl) methyloxy-1,2,4-triazolo [3,4-a]phthalazine in combination with nicotinic agonists, muscarinic agonists, and acetylcholinesterase inhibitors, in PCT International publications Nos. WO 99/47142, WO 99/47171, and WO 99/47131, respectively. Also see in this regard PCT International publication No. WO 99/37303 for its discussion of the use of a class of $GABA_A$ receptor ligands, 1,2,4-triazolo[4,3-b]pyridazines, in combination with SSRIs.

The invention also pertains to methods of inhibiting the binding of benzodiazepine compounds, such as Ro15-1788, to the $GABA_A$ receptors which methods involve contacting a compound of the invention with cells expressing $GABA_A$ receptors, wherein the compound is present at a concentration sufficient to inhibit benzodiazepine binding to $GABA_A$ receptors in vitro. This method includes inhibiting the binding of benzodiazepine compounds to $GABA_A$ receptors in vivo, e.g., in a patient given an amount of a compound of Formula I that would be sufficient to inhibit the binding of benzodiazepine compounds to $GABA_A$ receptors in vitro. In one embodiment, such methods are useful in treating benzodiazepine drug overdose. The amount of a compound that would be sufficient to inhibit the binding of a benzodiazepine compound to the $GABA_A$ receptor may be readily determined via an $GABA_A$ receptor binding assay, such as the assay described in Example 5. The $GABA_A$ receptors used to determine in vitro binding may be obtained from a variety of sources, for example from preparations of rat cortex or from cells expressing cloned human $GABA_A$ receptors.

The invention also pertains to methods for altering the signal-transducing activity, particularly the chloride ion conductance of $GABA_A$ receptors, said method comprising exposing cells expressing such receptors to an effective amount of a compound of the invention. This method includes altering the signal-transducing activity of $GABA_A$ receptors in vivo, e.g., in a patient given an amount of a compound of Formula I that would be sufficient to alter the signal-transducing activity of $GABA_A$ receptors in vitro. The amount of a compound that would be sufficient to alter the signal-transducing activity of $GABA_A$ receptors may be determined via a $GABA_A$ receptor signal transduction assay, such as the assay described in Example 6.

The $GABA_A$ receptor ligands provided by this invention and labeled derivatives thereof are also useful as standards and reagents in determining the ability of a potential pharmaceutical to bind to the $GABA_A$ receptor.

Labeled derivatives of the $GABA_A$ receptor ligands provided by this invention are also useful as radiotracers for positron emission tomography (PET) imaging or for single photon emission computerized tomography (SPECT).

The compounds herein described may have one or more asymmetric centers. Compounds of the invention containing an asymmetrically substituted atom may be isolated in enantiomerically enriched or racemic form. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent; derivatizing with an enantiomerically enriched resolving reagent, separating the resulting diastereomers through means well known in the art, and removing the enantiomerically enriched resolving reagent through ordinary chemical means such as, for example, hydrolysis or hydrogenation; or chromatography, using, for example a chiral HPLC column.

Many geometric isomers of olefins, carbon-nitrogen double bonds, and the like can also be present in the compounds described herein, and all such stable isomers are contemplated in the invention. Cis and trans geometric isomers, as well as E and Z isomers of the compounds of the invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

Some compounds of the invention exist as tautomers. Unless otherwise specified, any description or claim of one tautomeric form is intended to encompass the other tautomer.

The term "substituted", as used herein, means that any one or more hydrogens on the designated atom is replaced with a selection from the indicated group, provided that the designated atom's normal valence is not exceeded, and that the substitution results in a stable compound. When a substituent is keto (i.e., =O), then 2 hydrogens on the atom are replaced. Unless otherwise specified, when a group is substituted with more than one substituent, it is understood that the substituents are the same or different.

The invention includes all isotopes of atoms occurring in the compounds. Isotopes include those atoms having the same atomic number but different mass numbers. By way of general example and without limitation, isotopes of hydrogen include tritium and deuterium. Isotopes of carbon include $^{11}C$, $^{13}C$, and $^{14}C$.

When any variable occurs more than one time in any constituent or formula for a compound, its definition at each occurrence is independent of its definition at every other occurrence. Thus, for example, if a group is shown to be substituted with 0-2 R*, then said group may optionally be substituted with up to two R* groups and each R* is selected independently from the definition of R*. Also, combinations of substituents and/or variables are permissible only if such combinations result in stable compounds. Also, for example, dialkylamino groups are understood to contain two alkyl, preferably $C_1$-$C_6$ alkyl, groups that may be the same or different. Thus, dialkylamino encompasses N-ethyl-N-methylamino, N,N-diethylamino, N,N-dimethylamino, N-methyl-N-propylamino, and the like.

Where the term "alkyl" is used, either alone or within other terms such as "haloalkyl" and "alkylsulfonyl", it embraces linear and branched radicals having one to about twelve carbon atoms. Preferred alkyl radicals are "lower alkyl" radicals having one to about ten carbon atoms. More preferred are lower alkyl radicals having one to about six carbon atoms. Examples of alkyl include, but are not limited to, methyl, ethyl, n-propyl, iso-propyl, n-butyl, sec-butyl, tert-butyl, n-pentyl, and sec-pentyl and the like. Preferred alkyl groups are $C_1$-$C_6$ alkyl groups. Especially preferred alkyl groups are methyl, ethyl, propyl, butyl, 3-pentyl. The term $C_1$-$C_6$ alkyl as used herein includes alkyl groups having from 1 to 6 carbon atoms. Preferred examples are methyl and ethyl.

"Alkylsulfonyl" embraces alkyl groups attached to a sulfonyl radical, where alkyl is defined as above, i.e., a group of the formula —$SO_a$(alkyl). More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl.

The term "alkylsulfinyl" embraces radicals containing a linear or branched alkyl radical, of one to ten carbon atoms, attached to a divalent —S(=O)— atom.

The terms "N-alkylamino" and "N,N-dialkylamino" denote amino groups which have been substituted with one alkyl radical and with two alkyl radicals, respectively. More preferred alkylamino radicals are "lower alkylamino" radicals having one or two alkyl radicals of one to six carbon atoms, attached to a nitrogen atom. Suitable "alkylamino" may be mono or dialkylamino such as N-methylamino, N-ethylamino, N,N-dimethylamino, N,N-diethylamino or the like.

The term "alkylthio" embraces groups containing a linear or branched alkyl radical, of one to ten carbon atoms, attached to a divalent sulfur atom. An example of "alkylthio" is methylthio, ($CH_3$—S—).

The term "cycloalkyl" embraces radicals having three to ten carbon atoms. More preferred cycloalkyl radicals are "lower cycloalkyl" radicals having three to seven carbon atoms, i.e., $C_3$-$C_7$ cycloalkyl. Examples include radicals such as cyclopropyl, cyclobutyl, cyclopentyl, cyclohexyl and cycloheptyl.

In the term "$C_3$-$C_7$ cycloalkylalkyl", the $C_{3-7}$ cycloalkyl group is attached to the parent molecular moiety through the alkyl, preferably a $C_1$-$C_6$, more preferably a $C_1$-$C_4$ alkyl, group. This term encompasses, but is not limited to, cyclopropylmethyl, and cyclohexylmethyl.

By "carboxamido" as used herein is meant groups of the formula —C(O)NR'R" where R' and R" are the same or different and represent hydrogen or alkyl. Preferred carboxamido groups are those where both of R' and R" are hydrogen.

The term "alkenyl" embraces unsaturated straight and branched chain radicals having two to about ten carbon atoms. Such radicals contain at least one carbon-carbon double bond which may occur at any stable point along the chain. Examples of alkenyl groups include, but are not limited to such groups as ethenyl and propenyl.

The term "alkynyl" embraces straight and branched chain radicals having two to about ten carbon atoms and at least one carbon-carbon triple bond. The carbon-carbon triple bond may occur at any stable point along the chain. Examples of alkynyl groups include, but are not limited to such groups as ethynyl and propynyl.

"Alkoxy" represents an alkyl group as defined above attached to the parent molecular moiety through an oxygen bridge. Examples of alkoxy include, but are not limited to, methoxy, ethoxy, n-propoxy, iso-propoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, and 3-methylpentoxy. More preferred alkoxy groups include methoxy, ethoxy, isopropoxy, and isobutoxy.

As used herein, "alkanoyl" refers to an alkyl group as defined above attached through a carbonyl bridge, i.e., —CO(alkyl). Examples include acetyl, propionyl, and butyryl.

The term "aryl" is used to indicate aromatic groups that contain only carbon atoms in the ring structure. Thus, the term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups are, for example, phenyl, naphthyl, 1,2,3,4-tetrahydronaphthalene, indanyl, and biphenyl. Preferred aryl groups include phenyl, naphthyl, including 1-naphthyl and 2-naphthyl, and acenaphthyl. More preferred aryl groups include phenyl and napthyl. The aryl groups herein are unsubstituted or, as specified, substituted in one or more substitutable positions with various groups. Thus, such aryl groups are optionally substituted with, for example, $C_1$-$C_6$ alkyl, $C_1$-$C_6$ alkoxy, halogen, hydroxy, cyano, nitro, amino, mono- or di-($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono- or di($C_1$-$C_6$)alkylamino($C_1$-$C_6$)alkyl.

The term "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1). Examples of haloalkyl include, but are not limited to, trifluoromethyl, trichloromethyl, pentafluoroethyl, and pentachloroethyl. Preferred haloalkyl groups are halo($C_1$-$C_6$)alkyl groups; particularly preferred are trifluoromethyl, perfluoropropyl, and difluoromethyl.

By "haloalkoxy" as used herein is meant represents a haloalkyl group, as defined above, attached through an oxygen bridge to a parent group. Preferred haloalkoxy groups are halo($C_1$-$C_6$)alkoxy groups. Examples of haloalkoxy groups are trifluoromethoxy, 2,2-difluoroethoxy, 2,2,3-trifluoropropoxy and perfluoroisopropoxy.

Where the term "hydrocarbyl" is used, either alone or within other terms such as "hydrocarbylthio" and "hydrocarbylsulfinyl", it embraces straight, branched, and cyclic hydrocarbon groups having from 1 to about 12 carbon atoms. The hydrocarbyl groups are saturated or unsaturated, i.e., they contain one or more carbon-carbon double or triple bonds. Examples of hydrocarbyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, vinyl, isobutenyl, 2-pentenyl, 3-undecenyl, 4-nonenyl, acetylenyl, 2-methylpent-3-ynyl, 1-methyl-hex-2-ynyl, cyclopropylmethyl, cyclopropyl, cyclohexylmethyl, cyclohexyl and propargyl. When reference is made herein to $C_1$-$C_6$ hydrocarbyl containing one or two double or triple bonds it is understood that at least two carbons are present in the group for one double or triple bond, and at least four carbons for two double or triple bonds.

As used herein, the term "heteroaryl" means stable monocyclic, bicylclic and tricyclic ring systems which contain at least one aromatic ring where the aromatic ring contains from 5-7 members and from 1 to 4 hetero atoms independently selected from the group consisting of nitrogen, oxygen, and sulfur; the remaining rings contain from 5-7 members selected from carbon, oxygen, nitrogen, and sulfur. The aromatic ring containing a hetero atom is the "heteroaromatic ring." In bicyclic and tricyclic ring systems, the heteroaromatic ring may be fused to a carbocyclic ring that may be aromatic, such as benzo, or to a heteroaromatic ring, such as pyrido or pyrrolidino, or to heteroaromatic and one carbocyclic ring. Thus, "heteroaryl" includes ring systems having from one to three rings of from 5-7 ring members in each ring and where at least one ring is aromatic and contains from one to four hetero atoms. Any of the rings in the heteroaryl groups may be further fused to another ring forming a spiro ring system.

The nitrogen and sulfur heteroatoms may optionally be oxidized. The heterocyclic ring may be attached to its pendant group at any heteroatom or carbon atom which results in a stable structure. The heterocyclic rings described herein may be substituted on any substitutable carbon or nitrogen atom that results in a stable compound. Examples of suitable heteraryl substituents are $C_1$-$C_6$ alkyl, $C_1$-$C_6$ alkoxy, halogen, hydroxy, cyano, nitro, amino, mono- or di-($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, and mono- or di($C_1$-$C_6$)alkylamino($C_1$-$C_6$)alkyl.

Examples of heteroaryl groups include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, quinazolinyl, quinolinyl, 4H-quinolizinyl, quinoxalinyl, quinuclidinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred heteroaryl groups include, but are not limited to, pyridinyl, pyrimidinyl, furanyl, and thienyl.

As used herein, the term "heterocycloalkyl" is intended to mean a stable 5-to 7-membered monocyclic or 7- to 10-membered bicyclic ring system which contains at least one non-aromatic ring wherein said ring consists of carbon atoms and from 1 to 4 heteroatoms independently selected from the group consisting of N, O and S. The heterocycloalkyl ring or heterocycloalkyl bicyclic ring system may be fused to a benzene ring. A nitrogen in the heterocycle may optionally be quaternized. It is preferred that when the total number of S and O atoms in the heterocycloalkyl group exceeds 1, then these heteroatoms are not adjacent to one another. It is also preferred that the total number of S and 0 atoms in the heterocycloalkyl is not more than 1. Examples of heterocycloalkyl groups include but are not limited to tetrahydroquinolinyl, tetrahydroisoquinolinyl, pyrrolyl, piperazinyl, piperidinyl, tetrahydrofuranyl, morpholinyl, azetidinyl, 2H-pyrrolyl.

The term "halogen" indicates fluorine, chlorine, bromine, and iodine.

The term "—O—" represents an oxygen linker. Thus, the terms "—O-aryl" and "—O-heteroaryl" refer to aryl and heteroaryl groups as defined above connected though an oxygen atom to a parent molecular group. The terms "aryloxy" and "—O-aryl" are equivalent as used herein. In addition, the terms "heteroaryloxy" and "—O-heteroaryl" are equivalent as used herein.

Non-toxic pharmaceutically acceptable salts include, but are not limited to salts of inorganic acids such as hydrochloric, sulfuric, phosphoric, diphosphoric, hydrobromic, and nitric or salts of organic acids such as formic, citric, malic, maleic, fumaric, tartaric, succinic, acetic, lactic, methanesulfonic, p-toluenesulfonic, 2-hydroxyethylsulfonic, salicylic and stearic. Similarly, pharmaceutically acceptable cations include, but are not limited to sodium, potassium, calcium, aluminum, lithium and ammonium. Those skilled in the art will recognize a wide variety of non-toxic pharmaceutically acceptable addition salts. The invention also encompasses prodrugs of the compounds of Formula I.

The invention also encompasses the acylated prodrugs of the compounds of Formula I. Those skilled in the art will recognize various synthetic methodologies, which may be employed to prepare non-toxic pharmaceutically acceptable addition salts and acylated prodrugs of the compounds encompassed by Formula I.

Pharmaceutical Preparations

Those skilled in the art will recognize various synthetic methodologies that may be employed to prepare non-toxic pharmaceutically acceptable prodrugs of the compounds encompassed by Formula I. Those skilled in the art will also recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula I may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water.

It may be convenient to formulate these animal feed and drinking water compositions so that the animal ingests an appropriate quantity of the composition during a meal or throughout the course of the day. It may also be convenient to present the composition as a premix for addition to the feed or drinking water.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. For the treatment of anxiety, depression, or cognitive impairment a dosage regimen of 1 or 2 times daily is particularly preferred. For the treatment of sleep disorders a single dose that rapidly reaches effective concentrations is desirable.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have pharmacological properties that include, but are not limited to oral bioavailability, low toxicity, low serum protein binding and desirable in vitro and in vivo half-lives. Penetration of the blood brain barrier for compounds used to treat CNS disorders is necessary, while low brain levels of compounds used to treat peripheral disorders are often preferred.

Assays may be used to predict these desirable pharmacological properties. Assays used to predict bioavailability include transport across human intestinal cell monolayers, including Caco-2 cell monolayers. Toxicity to cultured hepatocytes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1-27).

Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120-1127).

Preparation of Compounds

A general illustration of the preparation of compounds of Formula I in the invention is given in Scheme I.

Scheme I

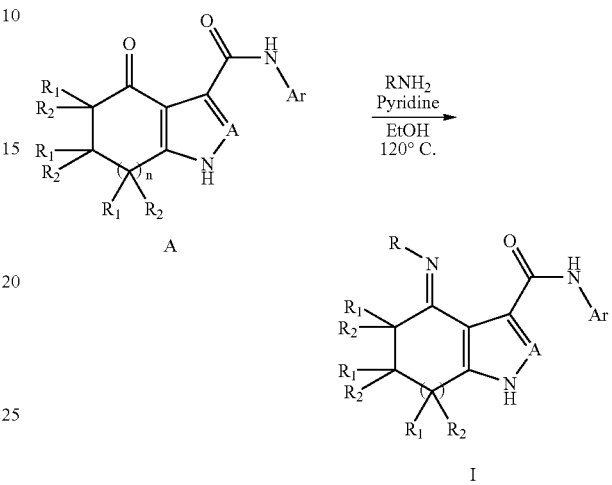

R, $R_1$, $R_2$, n, A and Ar are as defined in claim 1.

With respect to the preparation of the oximes of the invention (Scheme I), an appropriately substituted amine ($RNH_2$) is added to a suspension of the pyrrole or pyrazole carboxamide starting material in ethanol or other suitable solvent. The reaction mixture is heated for approximately 16 hours and the solvent is removed in vacuo to yield the oxime product (formula I).

The preparation of pyrrole carboxamides (formula A where A=$CR_3$) can be accomplished according to the procedures set forth in U.S. Pat. No. 5,804,686, which is hereby incorporated by reference. Suitable procedures are also described in U.S. patent application Ser. No. 09/387,311, filed Aug. 31, 1999, and U.S. patent application Ser. No. 09/651,207, filed Aug. 30, 2000, the disclosures of which are incorporated herein in their entirety. The preparation of such compounds is generally depicted in Scheme II. Also, see International Applications WO 97/2624 and WO 01/16103.

The preparation of pyrazole carboxamides (Formula A where A is nitrogen) can be accomplished according to the procedures set forth in International Application WO 00/40565.

Scheme II

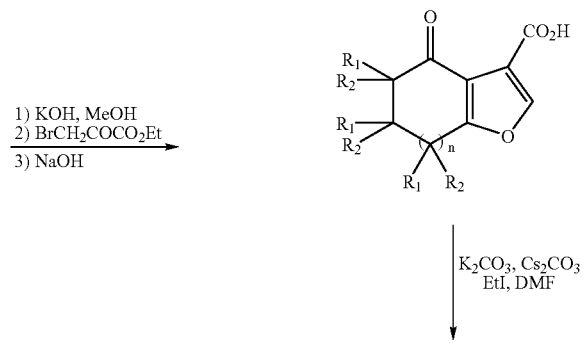

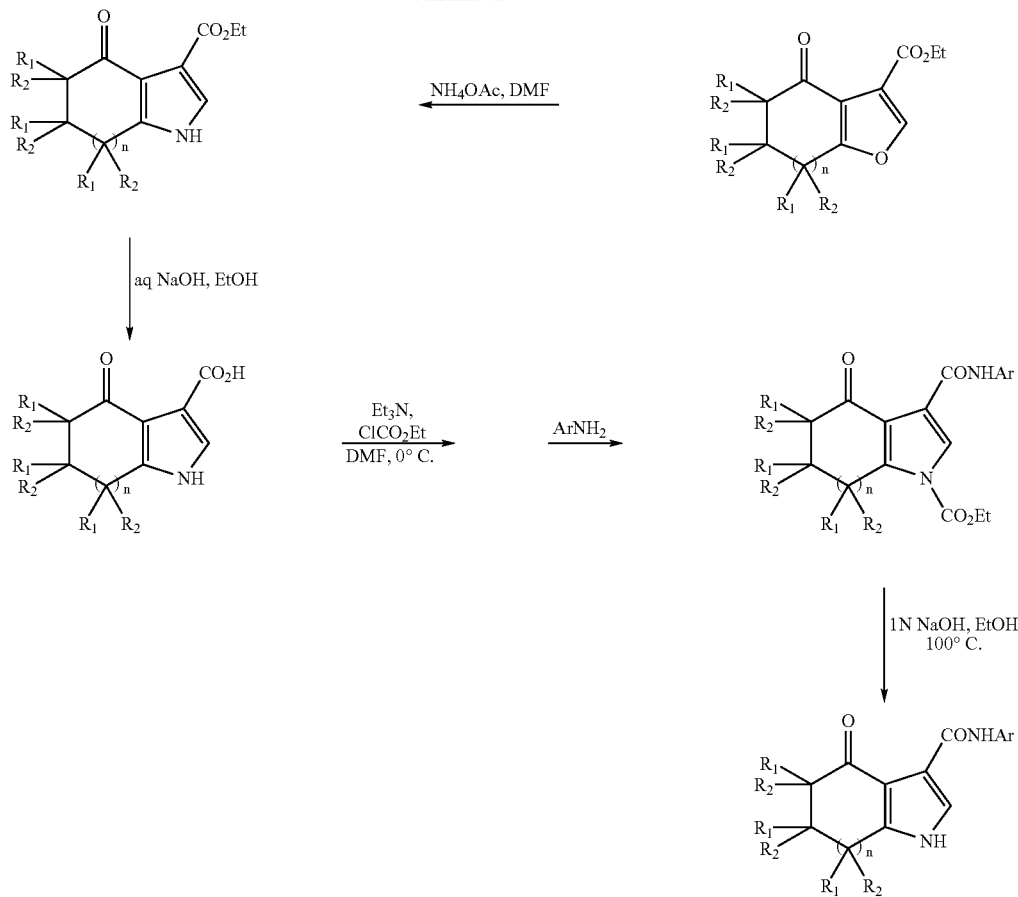
The preparation of representative Ar—NH$_2$ groups is (1) depicted below in Schemes III (1), (2) and (3).
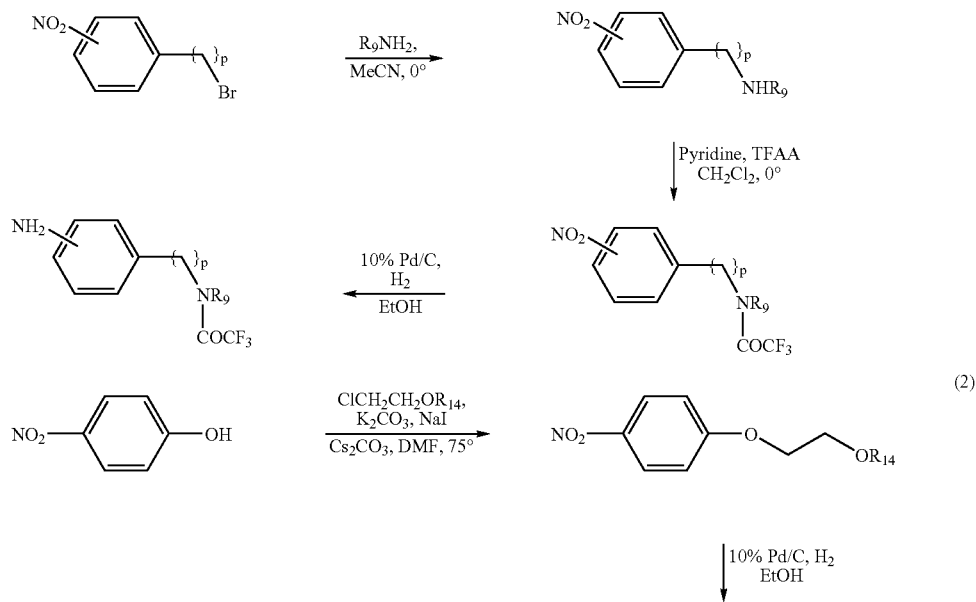

-continued

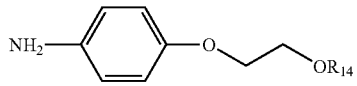

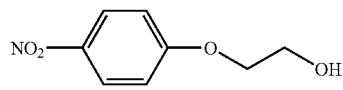 → 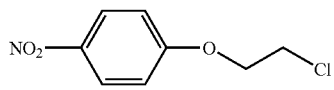

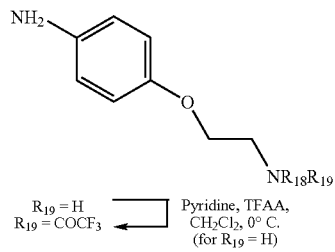 ← 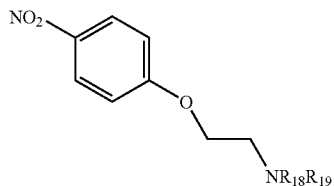

In Schemes III (1) and (2), $R_9$ and $R_{14}$ represent hydrogen or alkyl, preferably hydrogen or $C_1$-$C_6$ alkyl. In Scheme III(3), $R_{18}$ and $R_{19}$ independently represent hydrogen or alkyl, preferably hydrogen or $C_1$-$C_6$ alkyl, or $NR_{18}R_{19}$ represents a heterocycloalkyl group such as morpholinyl, piperidinyl, or piperazinyl.

The preparation of representative substituted pyridylamines useful as Ar—$NH_2$ groups for preparing compounds of Formula I as shown in Scheme II is depicted below in Scheme IV. In Scheme IV, $R_{30}$ represents hydrogen or hydrocarbyl substituted with up to two $R_A$ groups, preferably hydrogen or alkyl substituted with up to two $R_A$ groups.

Scheme IV

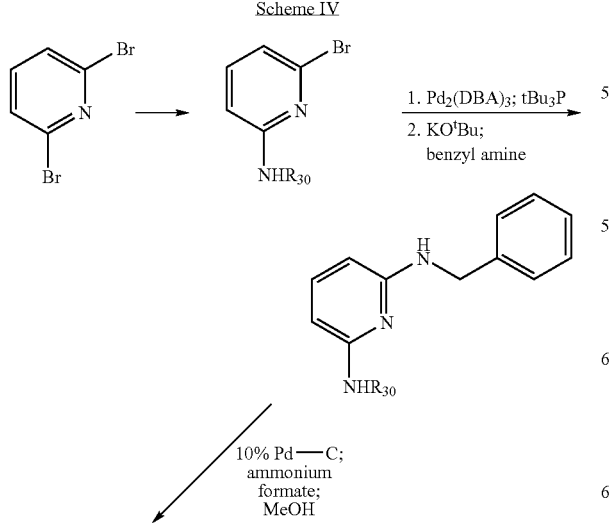

-continued

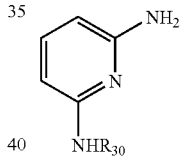

Scheme V

The preparation of other representative substituted anilines useful as Ar—$NH_2$ groups for preparing compounds of Formula I as shown in Scheme II is depicted below in Scheme V. In Scheme V, $R_{35}$ represents hydrogen or $C_1$-$C_6$ alkyl, preferably ethyl.

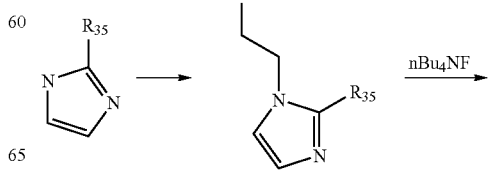

-continued

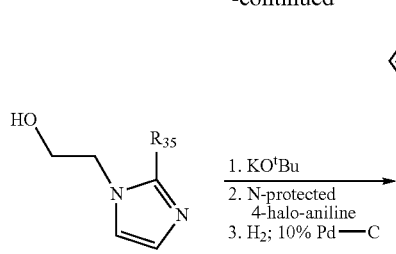

Those skilled in the art will recognize that it may be necessary to utilize different solvents or reagents to achieve some of the above transformations. Unless otherwise specified all reagents and solvent are of standard commercial grade and are used without further purification.

The disclosures in this application of all articles and references, including patents, are incorporated herein by reference in their entirety.

The invention is illustrated further by the following examples, which are not to be construed as limiting the invention in scope or spirit to the specific procedures described in them. Those having skill in the art will recognize that the starting materials may be varied and additional steps employed to produce compounds encompassed by the invention, as demonstrated by the following examples. In some cases, protection of reactive functionalities may be necessary to achieve some of the above transformations. In general, such need for protecting groups, as well as the conditions necessary to attach and remove such groups, will be apparent to those skilled in the art of organic synthesis.

EXAMPLES

Intermediates

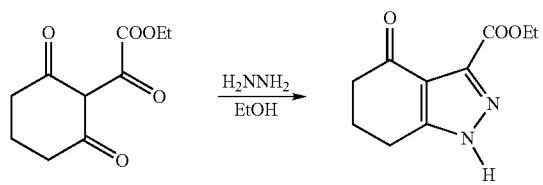

Example A

4-Oxo-4,5,6,7,4-tetrahydro-1H-indazole-3-carboxylic acid ethyl ester

A solution of 2-ethyloxalylcyclohexan-1,3-dione (*Synthesis*, 1976, 722) (9.50 g, 45 mmol), hydrazine monohydrate (2.2 mL, 45 mmol), and acetic acid (2.6 mL, 45 mmol) in ethanol (100 mL) is stirred at room temperature for 6 hours. The solvent is evaporated under reduced pressure and the resulting residue is dissolved in acetic acid (100 mL), heated to 120° C. and stirred under nitrogen for 3 hours. The reaction mixture is then cooled to about room temperature and concentrated. The concentrate is dissolved in chloroform (200 mL), treated with 10% NaCl (100 mL), and neutralized with 1 M sodium carbonate. The organic layer is separated, dried over $Na_2SO_4$, filtered and the solvent is evaporated to give 4-oxo-4,5,6,7,4-tetrahydro-1H-indazole-3-carboxylic acid ethyl ester (7.65 g, purity 90%, yield 73%). $^1$H NMR ($CDCl_3$) δ 0.95(t, J=7.1 Hz, 3 H), 2.17 (quintet, J=6.4 Hz, 2 H), 2.58 (t, J=6.8 Hz, 2 H), 3.00 (t, J=6.2 Hz, 2 H), 4.44 (q, J=7.3 Hz, 2 H). MW (Calc'd) 208.220; MS (M+H)$^+$ 209.

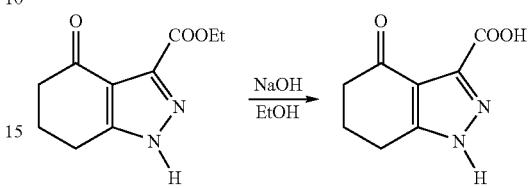

Example B

4-Oxo-4,5,6,7,4-tetrahydro-1H-indazole-3-carboxylic acid

A solution of 4-oxo-4,5,6,7-4-tetrahydro-1H-indazole-3-carboxylic acid ethyl ester (purity 90%, 1.84 g, 8.0 mmol) in methanol (20 mL) is treated with 10 N NaOH (4 mL) and stirred under nitrogen at 60° C. for 90 minutes. The reaction mixture is cooled to approximately room temperature and the solvent is evaporated under reduced pressure. The resulting residue is dissolved in water (30 mL), treated with brine (30 mL), and acidified to pH 2 with conc. hydrochloric acid to produce copious precipitate. The mixture is cooled to 0° C., filtered, the solid is washed with water (5 mL), and dried in a vacuum oven to give 4-oxo-4,5,6,7,4-tetrahydro-1H-indazole-3-carboxylic acid (0.99 g, 66%). $^1$H NMR (DMSO-$d_6$) δ 2.18 (quintet, J=6.2 Hz, 2 H), 2.66 (t, J=6.4 Hz, 2 H), 2.95 (t, J=6.2 Hz, 2 H).

Example C

4-Oxo-4,5,6,7,4-tetrahydro-1H-indazole-3-carboxylic acid 4-[2-(propylamino)ethoxy]phenylamide

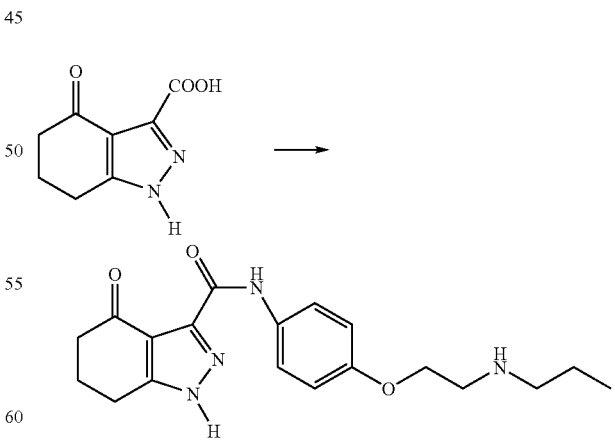

Ethyl chloroformate (0.24 mL, 2.5 mmol) is added to a −5° C. solution of 4-oxo-4,5,6,7,4-tetrahydro-1H-indazole-3-carboxylic acid (180 mg, 1.0 mmol) and triethylamine (0.56 mL, 4.0 mmol) in anhydrous DMF (3.0 mL). The mixture is stirred at 0° C. for 2 hours. [2-(4-Amino-phenoxy)-ethyl]-propyl-carbamic acid tert-butyl ester (294 mg, 1.0 mmol) is then added. The resulting mixture is stirred at room temperature for 16 hours and then at 50° C. for one hour. Methanol (2 mL) and 4 M KOH (1 mL) are then added, and the stirring at 50° C. is continued for an additional one hour. The reaction mixture is then poured into water (30 mL), neutralized with 1 M HCl, treated with 5% sodium bicarbonate (30 mL), and extracted with ethyl acetate (50 mL). The ethyl acetate layer is washed with water (50 mL), dried over magnesium sulfate, filtered and concentrated under reduced pressure. The residue is dissolved in chloroform (3 mL), treated with trifluoroacetic acid (2 mL), and stirred at room temperature for 3 hours. The reaction mixture is diluted with ethyl acetate (100 mL), washed with 1 M sodium carbonate (100 mL), dried over anhydrous sodium carbonate, filtered and concentrated under reduced pressure. The resulting crude product was purified by silica gel column chromatography using chloroform-methanol-acetic acid (80:16:4, v/v/v) as the eluent to give 95 mg (26%) of 4-oxo-4,5,6,7,4-tetrahydro-1H-indazole-3-carboxylic acid 4-[2-(propylamino)ethoxy]phenylamide. $^1$H NMR (CDCl$_3$) δ 0.95(t, J=7.3 Hz, 3 H), 1.68 (quintet, J=7.5 Hz, 2 H), 2.19 (m, 2 H), 2.65 (m, 2 H), 2.94 (t, J=7.5 Hz, 2 H), 3.00 (m, 2 H), 3.24 (m, 2 H), 4.28 (m, 2 H), 6.50 (bs, 2 H), 6.92 (d, J=9.0 Hz, 2 H), 7.69 (d, J=9.0 Hz, 2 H), 12.3 (s, 1 H). MW (calculated) 356.429; MS (M+H)$^+$ 357.

Example D

4-Oxo-4,5,6,7,4-tetrahydro-1H-indazole-3-carboxylic acid [3-fluoro-4-(2-(morpholin-4-yl-ethoxy)phenyl]-amide

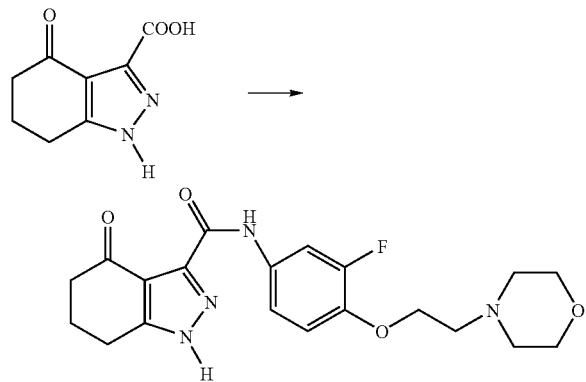

A mixture of 4-oxo-4,5,6,7,4-tetrahydro-1H-indazole-3-carboxylic acid (188 mg, 1.0 mmol), anhydrous DMF (4 mL), anhydrous dichloromethane (8 mL), 1-[3-(dimethylamino)propyl]-3-ethylcarbondiimide hydrochloride (287 mg, 1.5 mmol, DMAP (183 mg, 1.5 mmol), and 3-fluoro-4-(2-morpholin-4-yl-ethoxy)-phenylamine (288 mg, 1.2 mmol) is stirred under nitrogen at room temperature for 3 days. The reaction mixture is poured into 10% NaCl (50 mL) and extracted with chloroform (2×50 mL). The combined chloroform extracts are dried over Na$_2$CO$_3$, filtered and the solvent is evaporated under reduced pressure. The resulting residue is chromatographed on preparative silica gel plates using chloroform-methanol-acetic acid (70:24:6, v/v/v) as the eluent to give 130 mg (32%) of pure 4-oxo-4,5,6,7,4-tetrahydro-1H-indazole-3-carboxylic acid [3-fluoro-4-(2-(morpholin-4-yl-ethoxy)phenyl]-amide, as a white solid. $^1$H NMR (CD$_3$OD) δ 2.19 (quintet, J=6.0 Hz, 2 H), 2.65 (m, 6 H), 2.86 (t, J=5.5 Hz, 2 H), 2.95 (t, J=6.2 Hz, 2 H), 3.77 (t, J=4.6 Hz, 4 H), 4.20 (t, J=5.5 Hz, 2 H), 7.01 (t, J=9.0 Hz, 1 H), 7.36 (m, 1 H), 7.83 (dd, J=13.2 and 2.4 Hz, 1 H). MW 402.432 (calculated); MS (M+H)$^+$ 403.

Example E

4-Oxo-4,5,6,7-tetrahydro-1H-indazole-3-carboxylic acid [6-(2-propylamino-ethoxy)-pyridin-3-yl]-amide

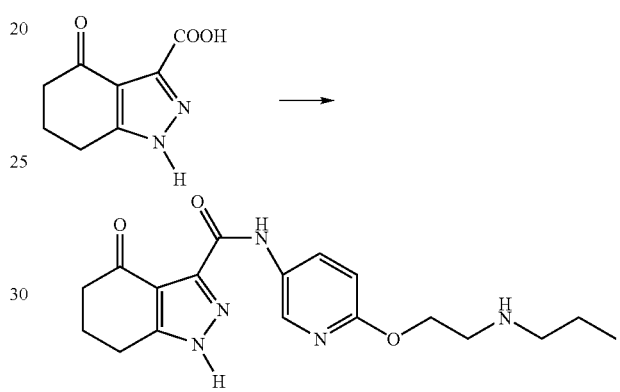

A mixture of 4-oxo-4,5,6,7,4-tetrahydro-1H-indazole-3-carboxylic acid (188 mg, 1.0 mmol), anhydrous DMF (4 mL), anhydrous dichloromethane (8 mL), 1-[3-(dimethylamino)propyl]-3-ethylcarbondiimide hydrochloride (287 mg, 1.5 mmol), DMAP (183 mg, 1.5 mmol), and [2-(5-amino-pyridin-2-yloxy)-ethyl]-propyl-carbamic acid tert-butyl ester (354 mg, 1.2 mmol) is stirred under nitrogen at room temperature for 3 days. The reaction mixture is then poured into 10% aqueous NaCl (50 mL) and extracted with chloroform (2×50 mL). The combined chloroform extracts are dried over Na$_2$CO$_3$, filtered and concentrated to afford a residue. The residue is dissolved in chloroform (10 mL), treated with trifluoroacetic acid (5 mL), and stirred under nitrogen at room temperature for 5 hours. The reaction mixture is evaporated under reduced pressure and the resulting residue is partitioned between chloroform (80 mL) and 1 M Na$_2$CO$_3$ (50 mL). The layers are separated and the chloroform layer is dried over anhydrous Na$_2$CO$_3$, filtered and concentrated. The concentrate was purified by preparative thin layer chromatography using 2000 µm silica gel plates and chloroform-methanol-acetic acid (70:24:6, v/v/v) as the eluent to give 150 mg (42%) of 4-oxo-4,5,6,7-tetrahydro-1H-indazole-3-carboxylic acid [6-(2-propylamino-ethoxy)-pyridin-3-yl]-amide as a white solid. $^1$H NMR (CDCl$_3$) δ 0.95 (t, J=7.3 Hz, 3 H), 1.70 (quintet, J=7.7 Hz, 2 H), 2.22 (t, J=6.1 Hz, 2 H), 2.67 (t, J=6.0 Hz, 2 H), 2.92 (t, J=7.5 Hz, 2 H), 3.06 (t, J=6.0 Hz, 2 H), 3.29 (t, J=4.9 Hz, 2 H), 4.51 (t, J=4.8 Hz, 2 H), 6.49 (d, J=8.8 Hz, 1 H), 7.80 (dd, J=8.8 and 2.6 Hz, 1 H), 8.62 (d, J=2.6 Hz, 1 H). MW 357.417 (calculated); MS (M+H)$^+$ 358, m.p. 120° C.

Example F

4-Oxo-4,5,6,7-tetrahydro-1H-indazole-3-carboxylic acid [6-(2-ethylamino-ethoxy)-pyridin-3-yl]-amide

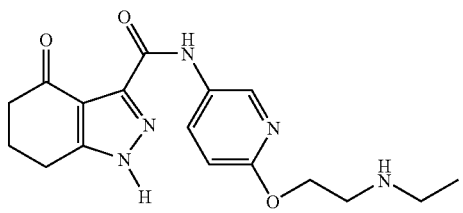

The title compound is obtained from a reaction of 4-oxo-4,5,6,7,4-tetrahydro-1H-indazole-3-carboxylic acid (188 mg, 1.0 mmol) with [2-(5-amino-pyridin-2-yloxy)-ethyl]-ethyl-carbamic acid tert-butyl ester (338 mg, 1.2 mmol) in the presence of 1-[3-(dimethylamino)propyl]-3-ethylcarbondiimide hydrochloride (287 mg, 1.5 mmol) and DMAP (183 mg, 1.5 mmol) using the procedure described above in Example 4. Yield: 120 mg (35%) of the desired product as a white solid. $^1$H NMR (CD$_3$OD) δ 1.17 (t, J=7.1 Hz, 3 H), 2.24 (quintet, J=6.4 Hz, 2 H), 2.70 (t, J=6.4 Hz, 2 H), 2.75 (q, J=7.0 Hz, 2 H), 2.98 (t, J=6.2 Hz, 2 H), 3.03 (t, J=5.1 Hz, 2 H), 4.41 (t, J=5.3 Hz, 2 H), 6.82 (d, J=9.0 Hz, 1 H), 8.11 (dd, J=8.8 and 2.4 Hz, 1 H). MW 343.390 (calc'd); MS (M+H)$^+$ 344.

Example G 4-oxo-4,5,6,7-tetrahydrobenzofuran-3-carboxylic acid

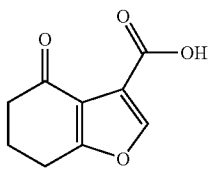

4-Oxo-4,5,6,7-tetrahydrobenzofuran-3-carboxylic acid is prepared according to the following procedure. Potassium hydroxide (345 g, 6.15 mol) is dissolved in methyl alcohol (1.2 L) then cooled in an ice water bath. A solution of cyclohexanedione (714 g, 6.15 mol) in methyl alcohol (1.2 L), dissolved using gentle heat, is added dropwise to the cold, stirred KOH solution over 2 h. A solution of ethyl bromopyruvate (1200 g, 6.15 mol) in methyl alcohol (1.5 L) is then added dropwise over 3 h. The reaction mixture is allowed to reach ambient temperature and stirred an additional 14.5 h. While cooling the reaction mixture via a water bath, a solution of sodium hydroxide (492 g, 12.4 mol) in water (984 mL) is added dropwise over 2.5 h. After stirring at ambient temperature for 15.5 h, the reaction mixture is cooled in an ice water bath, 500 g of ice added, and the resulting mixture is then acidified with concentrated hydrochloric acid (ca 1L) to pH 1. The reaction mixture is concentrated in vacuo, 1L of ice is added, and the precipitate filtered, washed with ice water (3×200 mL), and then dried in a vacuum oven at 75° C. to afford 4-oxo-4,5,6,7-tetrahydrobenzofuran-3-carboxylic acid (560 g). m.p. 137-138° C.

Example H 4-oxo-4,5,6,7-tetrahydroindole-3-carboxylate

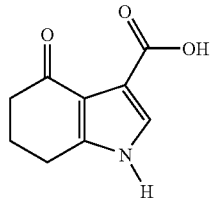

To a stirred mixture of 4-oxo-4,5,6,7-tetrahydrobenzofuran-3-carboxylic acid (640 g, 3.55 mol), potassium carbonate (1.7 kg, 10.65 mol) and cesium carbonate (100 g, 0.32 mol) in N,N-dimethylformamide (9.0 L) is added iodoethane (1250 g, 8.01 mol). The mixture is heated at 60° C. for 2 h. After cooling to ambient temperature, the mixture is filtered, the solid is rinsed with ethyl acetate, and the filtrate concentrated in vacuo. Water (2 L) is added then extracted with ethyl acetate (2×2 L); the combined organic extracts are washed with brine, dried over magnesium sulfate, filtered, and concentrated in vacuo to give ethyl 4-oxo-4,5,6,7-tetrahydrobenzofuran-3-carboxylic acid (642 g). A mixture of this ester (640 g, 3.07 mol) and ammonium acetate (426 g, 5.53 mol) in N,N-dimethylformamide (320 mL) is heated to 100° C. for 2 h. The reaction mixture is concentrated in vacuo, ice water (2.5 L) is added, and extracted with dichloromethane (2×3 L); the combined organic extracts are washed with brine, dried over magnesium sulfate, filtered, and concentrated in vacuo to give ethyl 4-oxo-4,5,6,7-tetrahydroindole-3-carboxylate (357 g). A mixture of this ester (170 g, 0.82 mol) in ethyl alcohol (250 mL) and a solution of sodium hydroxide (165 g, 4.1 mol) in water (1 L) is heated at reflux for 1 h, then cooled in an ice water bath. Concentrated hydrochloric acid (350 mL) is added dropwise, the precipitate collected by filtration, rinsed with ice water (3×), and dried in a vacuum oven at 75° C. to afford 4-oxo-4,5,6,7-tetrahydroindole-3-carboxylate (125 g). m.p. 269-270° C.

Example I

4-[N-trifluoroacetyl-(methylaminomethyl]aniline

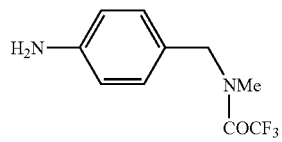

A solution of p-nitrobenzylbromide (5.40 g, 25 mmol) in acetonitrile (60 ml) is added dropwise to a stirred solution of aqueous methylamine (65 mL, 40 wt. %, 0.75 mol) in acetonitrile (50 mL) at 0° C. After stirring an additional 15 minutes, the solution is poured into brine and extracted 2× with dichloromethane. The combined organic layers are washed with brine, dried over sodium sulfate, filtered, and concentrated in vacuo to give 4-(methylaminomethyl)nitrobenzene (4.04 g).

A solution of trifluoracetic anhydride (4.46 mL, 31.6 mmol) in dichloromethane (10 mL) is added dropwise to a stirred solution of 4-(methylaminomethyl)nitrobenzene (4.04 g, 24.3 mmol) and pyridine (2.16 mL, 26.7 mmol) in dichloromethane (25 mL) at O0C. After stirring an additional 30 minutes, the solution is poured into aqueous 3.6N hydrochloric acid and extracted with dichloromethane. The organic layer is washed with brine, dried over sodium sulfate, filtered, and concentrated in vacuo to give 4-[N-trifluoroacetyl-(methylaminomethyl)]nitrobenzene (6.55 g).

Crude 4-[N-trifluoroacetyl-(methylaminomethyl)]nitrobenzene (6.55 g) is dissolved in ethyl alcohol (75 mL), added to 10% Pd/C (655 mg) in a Parr bottle and shaken under Hydrogen (50 PSI) for 4 hours. The mixture is filtered through Celite and concentrated in vacuo to give 4-[N-trifluoroacetyl-(methylaminomethyl)aniline (5.75 g).

Example J 4-amino-(N-trifluoroacetyl-2-methylaminoethoxy) benzene

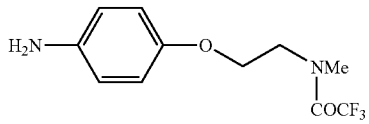

A mixture of p-nitrophenol (1.39 g, 10 mmol), 2-chloroethoxytrimethylsilane (3.2 ml, 20 mmol), potassium carbonate (4.15 g, 30 mmol), cesium carbonate (163 mg, 0.5 mmol), and sodium iodide (149 mg, 1 mmol) in N,N-dimethylformamide (10 ml) is heated at 75° C. for 19.5 hours. After cooling to ambient temperature, the mixture is diluted with ethyl acetate and filtered. The filtrate is washed with saturated aqueous sodium bicarbonate, then washed 2× with water, dried over magnesium sulfate, filtered, concentrated in vacuo, and purified on Silica gel (1:1 ethyl acetate/hexanes) to give 4-nitro-(2-Hydroxyethoxy)benzene (1.25 g).

4-Nitro-(2-Hydroxyethoxy)benzene (1.13 g, 6.2 mmol) in thionyl chloride (10 mL) is heated at reflux for 3 hours then concentrated in vacuo. After cooling the residue in an ice water bath, saturated aqueous sodium bicarbonate is added and the precipitate collected, rinsed with water, and dried to give 4-nitro-(2-chloroethoxy)benzene (909 mg).

A mixture of 4-nitro-(2-chloroethoxy)benzene (781 mg, 3.9 mmol) and aqueous methylamine (15 mL, 40 wt. %) in isopropyl alcohol (15 mL) is heated in a sealed tube at 100° for 4 hours. After cooling in an ice water bath, the mixture is poured into brine and extracted 2× with dichloromethane, dried over sodium sulfate, filtered, and concentrated in vacuo to give 4-nitro-(2-methylaminoethoxy)benzene (697 mg).

To a solution of 4-nitro-(2-methylaminoethoxy)benzene (766 mg, 3.9 mmol) and pyridine (0.35 mL, 4.29 mmol) in dichloromethane (5 mL) at 0° C. is added dropwise trifluoroacetic anhydride (0.72 mL, 5.08 mmol). After stirring at 0° C. for 3.5 hours, the mixture is poured into aqueous 1.2 N hydrochloric acid and extracted with dichloromethane. The organic layer is washed with saturated aqueous sodium bicarbonate then brine, dried over sodium sulfate, filtered, and concentrated in vacuo to give 4-nitro-(N-trifluoroacetyl-2-methylaminoethoxy)benzene (1.06 g). Treatment of this nitro compound with 10% Palladium on carbon in ethyl alcohol (18 mL) in a Parr bottle under Hydrogen (55 PSI) for 2.25 hours affords 4-amino-(N-trifluoroacetyl-2-methylaminoethoxy)benzene (709 mg).

Example K

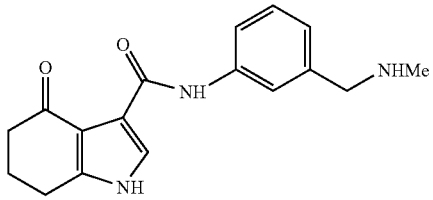

To a stirred solution of 4-oxo-4,5,6,7-tetrahydro-1H-indole-3-carboxylic acid (100 mg, 0.6 mmol) and triethylamine (0.15 mL, 1.1 mmol) in N,N-dimethylformamide (5 mL) at 0° C. is added ethyl chloroformate (0.1 mL, 1.1 mmol). After stirring an additional 1 hour, 3-(N-trifluoroacetyl-(methylaminomethyl)aniline (0.3 g, 1.3 mmol) is added. The reaction mixture is stirred for 4 hours, then poured into saturated aqueous ammonium chloride and extracted 2× with ethyl acetate. The combined organic layers are washed sequentially with brine, aqueous 2N hydrochloric acid, then brine, dried over sodium sulfate, filtered, and concentrated in vacuo. To the residue is added 15% aqueous potassium bicarbonate (5 mL) and methyl alcohol (3 mL), then heated at reflux for 3 hours. After cooling, the reaction mixture is extracted with ethyl acetate, the organic layer dried over sodium sulfate, filtered, and concentrated in vacuo to give N-[3-(methylaminomethyl)phenyl]-4-oxo-4,5,6,7-tetrahydro-1H-indole-3-carboxamide. m.p. 130-132° C.

Example L

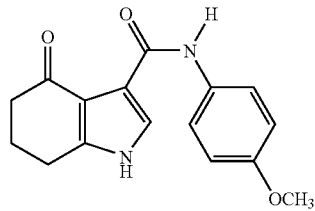

A mixture of 4-oxo-4,5,6,7-tetrahydro-1H-indole-3-carboxylic acid (179 mg, 1 mmol), P-anisidine (616 mg, 5 mmol), and 1-(3-dimethylaminopropyl)-3-ethylcarbodiimide hydrochloride [EDCI] (959 mg, 5 mmol) in 50% aqueous 1,4-dioxane (10 mL) was stirred at ambient temperature for 17 h. After concentrating in vacuo, the residue was taken up in 10% methanol in ethyl acetate, washed with 1.3M hydrochloric acid then with aqueous sodium bicarbonate, dried over magnesium sulfate, filtered, and concentrated in vacuo. Recrystallization from ethyl acetate afforded N-(4-methoxyphenyl)-4-oxo-4,5,6,7-tetrahydro-1H-indole-3-carboxamide (Compound 1); mp 219-220° C.

Example M

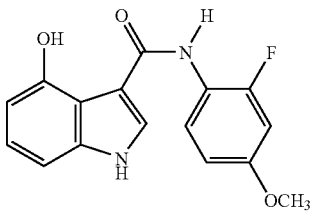

N-(2-Fluoro-4-methoxyphenyl)-4-benzyloxy-1H-indole-3-carboxamide (1.34 g, 3.4 mmol), prepared using the method above, was slurried with 10% palladium on carbon (134 mg) in ethanol (35 mL) in a Parr bottle and placed under a hydrogen atmosphere (50 psi) for 5 h. Methanol (5 ml) was added and the mixture returned to the Hydrogen atmosphere for an additional 18 h. The solution was filtered through Celite, concentrated in vacuo, and the residue purified by flash chromatography to afford N-(2-fluoro-4-methoxyphenyl)-4-hydroxy-1H-indole-3-carboxamide (Compound 2) as a beige solid; mp 259-261° C. (d).

Example N

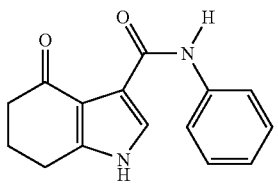

A mixture of 4-oxo-4,5,6,7-tetrahydro-1H-indole-3-carboxylic acid (179 mg, 1 mmol), aniline (0.46 mL, 5^ mmol), and 1-(3-dimethylaminopropyl)-3-ethylcarbodiimide hydrochloride (959 mg, 5 mmol) in 50% aqueous dioxane (10 mL) was allowed to stir at ambient temperature for 17.5 hours, then concentrated in vacuo. The residue was cooled in an ice water bath, aqueous 3.6 N hydrochloric acid was added, and the precipitate collected, rinsed with aqueous 3.6 N hydrochloric acid then water and dried. Recrystallization from ethyl alcohol afforded N-phenyl-4-oxo-4,5,6,7-tetrahydro-1H-indole-3-carboxamide (Compound 35) (164 mg). mp 225-226° C.

Example O

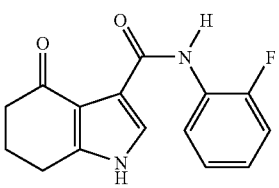

To a solution of 4-oxo-4,5,6,7-tetrahydro-1H-indole-3-carboxylic acid (538 mg, 3 mmol) and triethylamine (0.88 mL, 6.3 mmol) in N,N-dimethylformamide (15 mL) at 0° C. was added ethyl chloroformate (0.57 mL, 6 mmol). After stirring at 0° C. for 45 minutes, 2-fluoroaniline (0.58 mL, 6 mmol) wad added. The mixture was stirred for an additional 45 minutes, then allowed to stir at ambient temperature for 14 hours. The mixture was poured into aqueous 1.2 N hydrochloric acid and extracted 2× with ethyl acetate. The combined organic layers were washed with water, dried over magnesium sulfate, filtered, and concentrated in vacuo. To the residue was added aqueous 1N sodium hydroxide (10 mL) and ethyl alcohol (2 mL) and the mixture heated at reflux for 4.5 hours. After cooling in an ice water bath, the mixture was acidified with aqueous hydrochloric acid, the precipitate collected, rinsed with water and dried. Recrystallization from ethyl alcohol afforded N-(2-fluorophenyl)-4-oxo-4,5,6,7-tetrahydro-1H-indole-3-carboxamide (Compound 46) (530 mg). mp 238-240° C.

Example 1

Preparation of 4-methoxyimino-4,5,6,7-tetrahydro-1H-indole-3-carboxylic acid (2-fluoro-phenyl)-amide

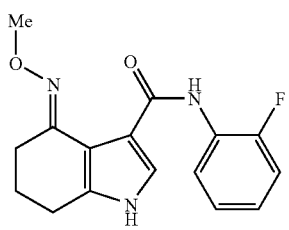

4-oxo-4,5,6,7-tetrahydro-1H-indole-3-carboxylic acid (2-fluoro-phenyl)-amide (0.73 mmol), pyridine (2.2 mmol), EtOH (10 ml) and methoxylamine hydrochloride (2.2 mmol) are combined in a sealed tube and heated at 120° C. for 16 hours. The reaction mixture is cooled to room temperature, the solvent is removed in vacuo and the residue is treated with 10 ml of $H_2O$ for 5 minutes. The resulting solid is collected by vacuum filtration to yield 160 mg (72%) of 4-methoxyimino-4,5,6,7-tetrahydro-1H-indole-3-carboxylic acid (2-fluoro-phenyl)-amide as a white solid. $^1$H NMR (DMSO-d$^6$) δ 1.80-1.86 (m, 2H), 2.62-2.73 (m, 4H), 3.81 (s, 3H), 7.10-7.29 (m, 3H), 7.48 (d, 1H), 8.01 (t, 1H), 11.70 (s, 1H), 11.81 (s, 1H).

Example 2

The following compounds (shown in Table 1) are prepared essentially according to the procedures shown in Schemes I-V and further illustrated in the Examples.

TABLE 1

[Structure: 4,5,6,7-tetrahydro-1H-indazole-3-carboxamide core with R-N= at 4-position, C(=O)-NH-Ar at 3-position, A in 5-membered ring]

| Example Number | R | A | Ar | Compound Name | $^1$H NMR chemical shift |
|---|---|---|---|---|---|
| 1 | 4-propyl-phenyl (CH₂CH₂CH₃-C₆H₄-) | N | 4-propyl-phenyl | 4-(4-Propyl-phenylimino)-4,5,6,7-tetrahydro-1H-indazole-3-carboxylic acid (4-propyl-phenyl)-amide | |
| 2 | (CH₃)₂CH— | N | 3-fluoro-4-methoxy-phenyl | 4-Isopropylimino-4,5,6,7-tetrahydro-1H-indazole-3-carboxylic acid (3-fluoro-4-methoxy-phenyl)-amide | |
| 3 | (CH₃)O— | CH | 2-fluoro-phenyl | 4-Methoxyimino-4,5,6,7-tetrahydro-1H-indole-3-carboxylic acid (2-fluoro-phenyl)-amide | |
| 4 | CH₃CH₂O— | CH | 2-fluoro-phenyl | 4-Ethoxyimino-4,5,6,7-tetrahydro-1H-indole-3-carboxylic acid (2-fluoro-phenyl)-amide | (CDCl₃) 1.22 (t, 3H), 1.91–1.95 (m, 2H), 2.63 (t, 2H), 2.80 (t, 2H), 4.20 (q, 2H), 7.10–7.18 (m, 3H), 7.60 (s, 1H), 8.03 (t, 1H), 9.82 (s, 1H), 12.20 (s, 1H) |
| 5 | (CH₃)₂CHO— | CH | 2-fluoro-phenyl | 4-(2-propoxy)imino-4,5,6,7-tetrahydro-1H-indole-3-carboxylic acid (2-fluoro-phenyl-amide | (CDCl₃) 1.21 (d, 6H), 1.87–1.94 (m, 2H), 2.63 (t, 2H), 2.77 (t, 2H), 4.42–4.49 (m, 1H), 7.09–7.16 (m, 3H), 7.59 (d, 1H), 7.94 (t, 1H), 9.88 (s, 1H0, 12.20 (s, 1H) |
| 6 | (CH₃)O— | N | 4-(2-propylamino-ethoxy)-phenyl | 4-Methoxyimino-4,5,6,7-tetrahydro-1H-indazole-3-carboxylic acid [4-(2-propylamino-ethoxy)-phenyl]-amide | |

TABLE 1-continued

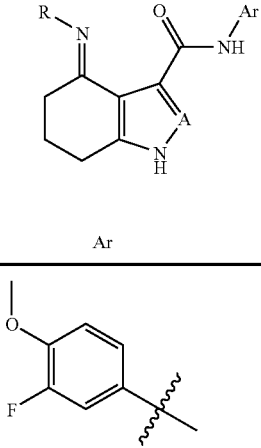

| Example Number | R | A | Ar | Compound Name | ¹H NMR chemical shift |
|---|---|---|---|---|---|
| 7 | (CH$_3$)O— | CH | 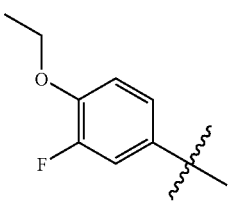 | 4-Methoxyimino-4,5,6,7-tetrahydro-1H-indole-3-carboxylic acid (3-fluoro-4-methoxy-phenyl)-amide | (DMSO-d$^6$) 1.81–1.86 (m, 2H), 2.63–2.72 (m, 4H), 3.81 (s, 3H), 3.97 (s, 3H), 7.18 (t, 1H), 7.22 (d, 1H), 7.27 (d, 1H), 7.72 (d, 1H), 11.68 (s, 1H), 11.90 (s, 1H) |
| 8 | (CH$_3$)O— | CH | 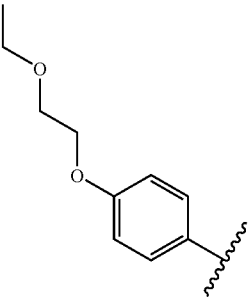 | 4-Methoxyimino-4,5,6,7-tetrahydro-1H-indole-3-carboxylic acid (3-fluoro-4-ethoxy-phenyl)-amide | (DMSO-d$^6$) 1.33 (t, 3H), 1.80–1.87 (m, 2H), 2.62–2.72 (m, 4H), 3.98 (s, 3H), 4.06 (q, 2H), 7.10 (t, 1H), 7.20 (d, 1H), 7.46 (d, 1H), 7.75 (d, 1H), 11.67 (s, 1H), 11.90 (s, 1H) |
| 9 | (CH$_3$)O— | CH | 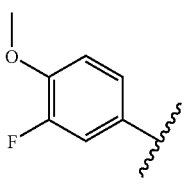 | 4-Methoxyimino-4,5,6,7-tetrahydro-1H-indole-3-carboxylic acid [4-(2-ethoxy-ethoxy)-phenyl]-amide | (DMSO-d$^6$) 1.12 (t, 3H), 1.80–2.85 (m, 2H), 2.63–2.72 (m, 4H), 3.50 (q, 2H), 3.68 (t, 2H), 3.97 (s, 3H), 4.03 (t, 2H), 6.62 (d, 1H), 7.18 (d, 1H), 7.21 (t, 1H), 7.41 (s, 1H), 7.47 (s, 1H), 11.68 (s, 1H), 11.82 (s, 1H) |
| 10 | (CH$_3$)O— | N | 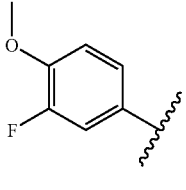 | 4-Methoxyimino-4,5,6,7-tetrahydro-1H-indazole-3-carboxylic acid (3-fluoro-4-methoxy-phenyl)-amide | |
| 11 | CH$_3$CH$_2$O— | N | 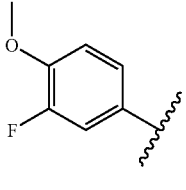 | 4-Ethoxyimino-4,5,6,7-tetrahydro-1H-indazole-3-carboxylic acid (3-fluoro-4-methoxy-phenyl)-amide | |
| 12 | (CH$_3$)O— | N | 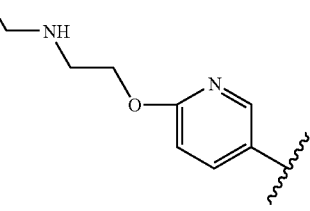 | 4-Methoxyimino-4,5,6,7-tetrahydro-1H-indazole-3-carboxylic acid [6-(2-propylamino-ethoxy)-pyridin-3-yl]amide | |

TABLE 1-continued

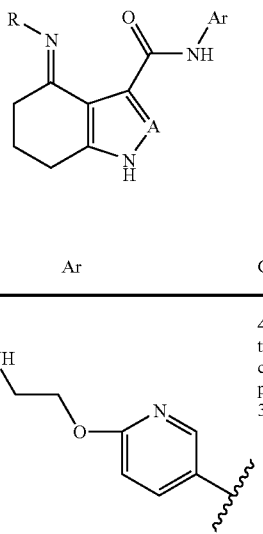

| Example Number | R | A | Ar | Compound Name | $^1$H NMR chemical shift |
|---|---|---|---|---|---|
| 13 | CH₃CH₂O— | N | 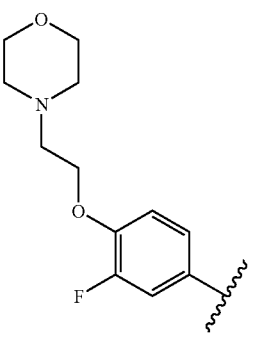 | 4-Ethoxyimino-4,5,6,7-tetrahydro-1H-indazole-3-carboxylic acid [6-(2-propylamino-ethoxy)-pyridin-3-yl]-amide | |
| 14 | (CH₃)O— | N | 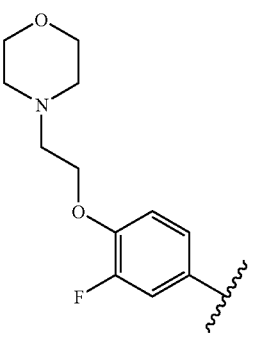 | 4-Methoxyimino-4,5,6,7-tetrahydro-1H-indazole-3-carboxylic acid [4-(2-morpholin-4-yl-ethoxy)-3-fluorophenyl]-amide | |
| 15 | CH₃CH₂O— | N | | 4-Ethoxyimino-4,5,6,7-tetrahydro-1H-indazole-3-carboxylic acid [4-(2-morpholin-4-yl-ethoxy)-3-fluorophenyl]-amide | |
| 16 | (CH₃)O— | N | 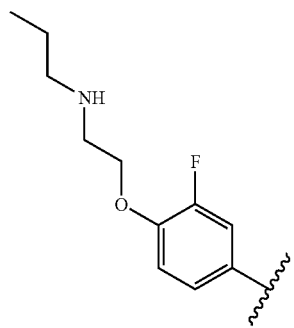 | 4-Methoxyimino-4,5,6,7-tetrahydro-1H-indazole-3-carboxylic acid [4-(2-propylamino-ethoxy)-3-fluoro-phenyl]-amide | |

TABLE 1-continued

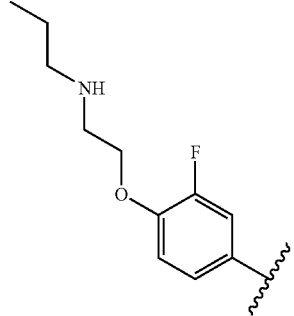

| Example Number | R | A | Ar | Compound Name | $^1$H NMR chemical shift |
|---|---|---|---|---|---|
| 17 | CH$_3$CH$_2$O— | N | 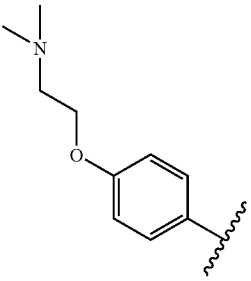 | 4-Ethoxyimino-4,5,6,7-tetrahydro-1H-indazole-3-carboxylic acid [4-(2-propylamino-ethoxy)-3-fluoro-phenyl]-amide | |
| 18 | CH$_3$CH$_2$O— | N | 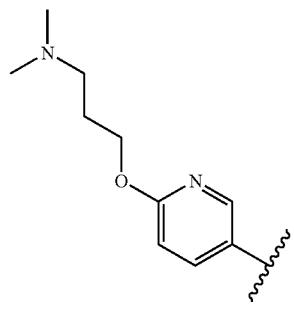 | 4-Ethoxyimino-4,5,6,7-tetrahydro-1H-indazole-3-carboxylic acid [4-(2-dimethylamino-ethoxy)-phenyl]-amide | |
| 19 | HO— | N | 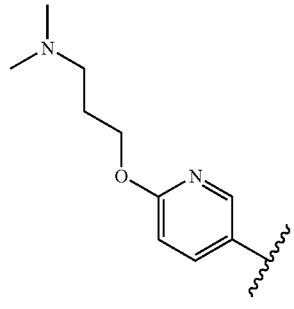 | 4-Hydroxyimino-4,5,6,7-tetrahydro-1H-indazole-3-carboxylic acid [6-(3-dimethylamino-propoxy)-pyridin-3-yl]-amide | |
| 20 | (CH$_3$)O— | N | | 4-Methoxyimino-4,5,6,7-tetrahydro-1H-indazole-3-carboxylic acid [6-(3-dimethylamino-propoxy)-pyridin-3-yl]-amide | |

TABLE 1-continued

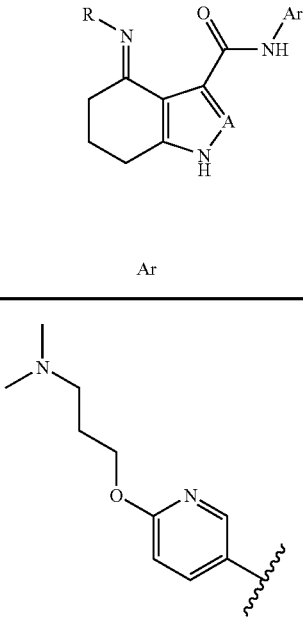

| Example Number | R | A | Ar | Compound Name | $^1$H NMR chemical shift |
|---|---|---|---|---|---|
| 21 | $CH_3CH_2O-$ | N | 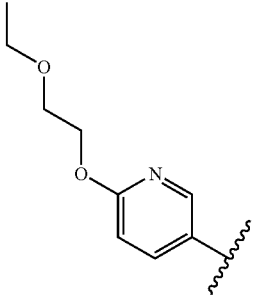 | 4-Ethoxyimino-4,5,6,7-tetrahydro-1H-indazole-3-carboxylic acid [6-(3-dimethylamino-propoxy)-pyridin-3-yl]-amide | |
| 22 | $CH_3O-$ | N | 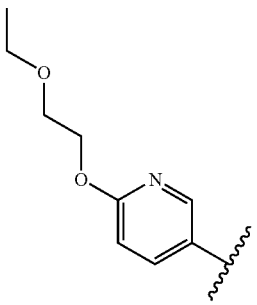 | 4-Methoxyimino-4,5,6,7-tetrahydro-1H-indazole-3-carboxylic acid [6-(2-ethoxy-ethoxy)-pyridin-3-yl]-amide | |
| 23 | $CH_3CH_2O-$ | N | | 4-Ethoxyimino-4,5,6,7-tetrahydro-1H-indazole-3-carboxylic acid [6-(2-ethoxy-ethoxy)-pyridin-3-yl]-amide | |
| 24 | $CH_3O-$ | N | 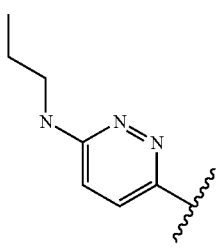 | 4-Methoxyimino-4,5,6,7-tetrahydro-1H-indazole-3-carboxylic acid (6-propylamino-pyridazin-3-yl)-amide | |

TABLE 1-continued

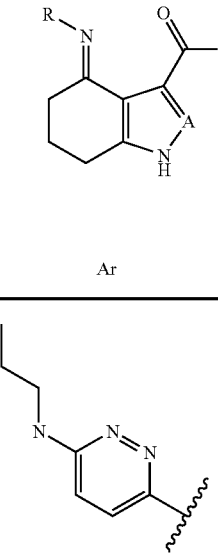

| Example Number | R | A | Ar | Compound Name | ¹H NMR chemical shift |
|---|---|---|---|---|---|
| 25 | CH₃CH₂O— | N | 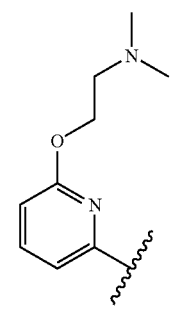 | 4-Ethoxylimino-4,5,6,7-tetrahydro-1H-indazole-3-carboxylic acid (6-propylamino-pyridazin-3-yl)-amide | |
| 26 | CH₃CH₂O— | N | 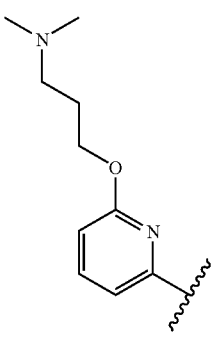 | 4-Ethoxyimino-4,5,6,7-tetrahydro-1H-indazole-3-carboxylic acid [6-(2-dimethylamino-ethoxy)-pyridin-2-yl]-amide | |
| 27 | CH₃CH₂O— | N | | 4-Ethoxyimino-4,5,6,7-tetrahydro-1H-indazole-3-carboxylic acid [6-(3-dimethylamino-propoxy)-pyridin-2-yl]-amide | |
| 28 | CH₃O— | N | 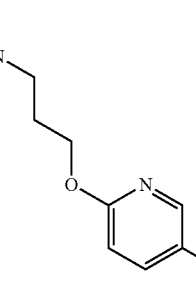 | 4-Methoxyimino-4,5,6,7-tetrahydro-1H-indazole-3-carboxylic acid [6-(3-diethylamino-propoxy)-pyridin-3-yl]-amide | |

TABLE 1-continued

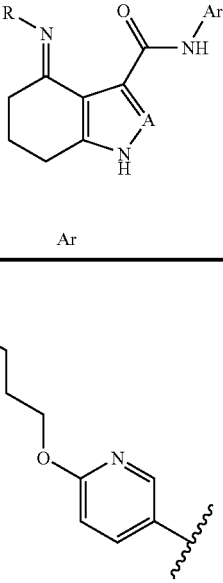

| Example Number | R | A | Ar | Compound Name | $^1$H NMR chemical shift |
|---|---|---|---|---|---|
| 29 | CH₃CH₂O— | N | 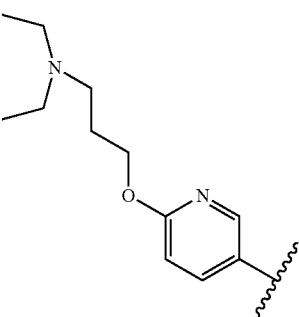 | 4-Ethoxyimino-4,5,6,7-tetrahydro-1H-indazole-3-carboxylic acid [6-(3-diethylamino-propoxy)-pyridin-3-yl]-amide | |
| 30 | HO— | N | 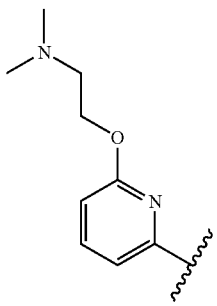 | 4-Hydroxyimino-4,5,6,7-tetrahydro-1H-indazole-3-carboxylic acid [6-(3-diethylamino-propoxy)-pyridin-3-yl]-amide | |
| 31 | CH₃O— | N | | 4-Methoxyimino-4,5,6,7-tetrahydro-1H-indazole-3-carboxylic acid [6-(3-dimethylamino-ethoxy)-pyridin-2-yl]-amide | |
| 32 | CH₃O— | N | 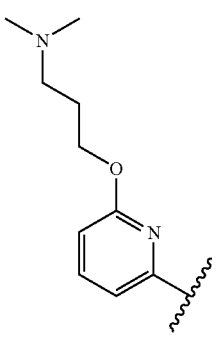 | 4-Methoxyimino-4,5,6,7-tetrahydro-1H-indazole-3-carboxylic acid [6-(3-dimethylamino-propoxy)-pyridin-2-yl]-amide | |

Example 3

Preparation of Radiolabeled Probe Compounds of the Invention

The compounds of the invention are prepared as radiolabeled probes by carrying out their synthesis using precursors comprising at least one atom that is a radioisotope. The radioisotope is preferably selected from of at least one of carbon (preferably $^{14}C$), hydrogen (preferably $^{3}H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph. In addition, tritium may also be introduced by tritium-halogen exchange with tritium gas, transition metal catalyzed tritium gas reduction of unsaturated bonds, or sodium borotritide reduction of ketones, aldehydes, and imines.

Example 4

Receptor Autoradiography

Receptor autoradiography (receptor mapping) is carried out in vitro as described by Kuhar in sections 8.1.1 to 8.1.9 of Current Protocols in Pharmacology (1998) John Wiley & Sons, New York, using radiolabeled compounds of the invention prepared as described in the preceding Example.

Example 5

Binding Assay

This assay is a standard assay for $GABA_A$ binding affinity. The high affinity and high selectivity of compounds of this invention for the benzodiazepine site of the $GABA_A$ receptor is confirmed using the binding assay described in Thomas and Tallman (*J. Bio. Chem.* 1981; 156:9838-9842, and *J. Neurosci.* 1983; 3:433-440).

Rat cortical tissue is dissected and homogenized in 25 volumes (w/v) of Buffer A (0.05 M Tris HCl buffer, pH 7.4 at 4° C.). The tissue homogenate is centrifuged in the cold (4° C.) at 20,000×g for 20 minutes. The supernatant is decanted, the pellet rehomogenized in the same volume of buffer, and centrifuged again at 20,000×g. The supernatant of this centrifugation step is decanted and the pellet stored at −20° C. overnight. The pellet is then thawed, resuspended in 25 volumes of Buffer A (original wt/vol), centrifuged at 20,000×g and the supernatant is then decanted. This wash step is repeated once. The pellet is finally resuspended in 50 volumes of Buffer A.

Incubations containing 100 µl of tissue homogenate, 100 µl of radioligand, (0.5 nM $^{3}H$-Ro15-1788 [$^{3}H$-Flumazenil], specific activity 80 Ci/mmol), and test compound or control (see below), and are brought to a total volume of 500 µl with Buffer A. Incubations are carried for 30 min at 4° C. and then rapidly filtered through Whatman GFB filters to separate free and bound ligand. Filters are washed twice with fresh Buffer A and counted in a liquid scintillation counter. Nonspecific binding (control) is determined by displacement of $^{3}H$ Ro15-1788 with 10 µM Diazepam (Research Biochemicals International, Natick, Mass.). Data were collected in triplicate, averaged, and percent inhibition of total specific binding (Total Specific Binding=Total−Nonspecific) was calculated for each compound.

A competition binding curve is obtained with up to 11 points spanning the compound concentration range from $10^{-12}M$ to $10^{-5}M$ obtained per curve by the method described above for determining percent inhibition. $K_i$ values are calculated according the Cheng-Prussof equation. When tested using this assay, preferred compounds of Formula I exhibit $K_i$ values of less than 1 uM, more preferred compounds of the invention have $K_i$ values of less than 500 nM, and particularly preferred compounds have $K_i$ values of less than 100 nM. Compounds 11-32 exhibit $K_i$ values of less than 1 uM.

Example 6

Electrophysiology

The following assay is used to determine if a compound of the invention act as an agonist, an antagonist, or an inverse agonist at the benzodiazepine site of the $GABA_A$ receptor.

Assays are carried out as described in White and Gurley (NeuroReport 6: 1313-1316, 1995) and White, Gurley, Hartnett, Stirling, and Gregory (Receptors and Channels 3: 1-5, 1995) with modifications. Electrophysiological recordings are carried out using the two electrode voltage-clamp technique at a membrane holding potential of −70 mV. *Xenopus Laevis* oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\beta_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$, GENBANK accession no. X15467; rat $\beta_3$, GENBANK accession no. X15468; and rat $\gamma_2$, GENBANK accession no. L08497. For each subunit combination, sufficient message for each constituent subunit is injected to provide current amplitudes of >10 nA when 1 µM GABA is applied.

Compounds are evaluated against a GABA concentration that evokes <10% of the maximal evokable GABA current (e.g. 1 µM–9 µM). Each oocyte is exposed to increasing concentrations of compound in order to evaluate a concentration/effect relationship. Compound efficacy is calculated as a percent-change in current amplitude: $100*((Ic/I)-1)$, where Ic is the GABA evoked current amplitude observed in the presence of test compound and I is the GABA evoked current amplitude observed in the absence of the test compound.

Specificity of a compound for the benzodiazepine site is determined following completion of a concentration/effect curve. After washing the oocyte sufficiently to remove previously applied compound, the oocyte is exposed to GABA+1 μM RO15-1788, followed by exposure to GABA+1 μM RO15-1788+test compound. Percent change due to addition of compound is calculated as described above. Any percent change observed in the presence of RO15-1788 is subtracted from the percent changes in current amplitude observed in the absence of 1 μM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A compound of the formula:

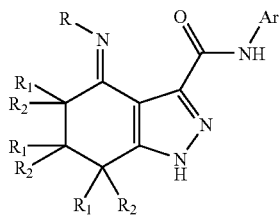

or a pharmaceutically acceptable salt thereof, wherein:
R is hydroxy, alkyl or alkoxy, where each alkyl is optionally substituted with oxo, haloalkyl, haloalkoxy, halogen, cyano, hydroxy, alkyl, nitro, azido, alkanoyl, carboxamido, alkoxy, aryloxy, alkylthio, alkylsulfinyl, alkylsulfonyl, amino, mono or dialkylamino, aryl, arylalkyl, arylalkoxy, heteroaryl or heterocycloalkyl; or
R is —O-aryl or aryl, each of which is optionally substituted with halogen, cyano, hydroxyl, nitro, azido, alkanoyl, carboxamido, alkyl, alkoxy, aryloxy, haloalkyl, haloalkoxy, alkylthio alkylsulfinyl, alkylsulfonyl, amino, mono or di(alkyl)amino, aryl, arylalkyl, arylalkoxy, heteroaryl or heterocycloalkyl;
wherein each alkyl is optionally substituted with 1, 2, 3, 4, or 5 substituents independently selected from the group consisting of oxo, halogen, cyano, nitro, haloalkyl, haloalkoxy, hydroxy, amino, alkyl substituted with 0-2 $R_A$, alkoxy substituted with 0-2 $R_A$, —NH(alkyl) substituted with 0-2 $R_A$, —N(alkyl)(alkyl) where each alkyl is independently substituted with 0-2 $R_A$, phenyl substituted with 0-3 $R_A$, —$XR_B$, and $R_C$; wherein
$R_A$ is independently selected at each occurrence from the group consisting of halogen, hydroxy, alkyl, alkoxy, —NH(alkyl), —N(alkyl)(alkyl) heterocycloalkyl, —S(O)$_m$(alkyl), where m is 0, 1, or 2, haloalkyl, haloalkoxy, —CO(alkyl), —CONH(alkyl), —CON(alkyl)(alkyl), —$XR_B$, and Y;

X is independently selected at each occurrence from the group consisting of —CH$_2$—, —CHR$_C$—, —O—, —S(O)$_g$, —NH—, —NR$_C$—, —C(=O)—, —C(=O)O—, —C(=O)NH—, —C(=O)NR$_C$—, —S(O)$_g$NH—, —S(O)$_g$NR$_C$—, NHC(=O)—, —NR$_C$C(=O)—, —NHS(O)$_g$—, and —NR$_C$S(O)$_g$—; where g is 0, 1, or 2;

$R_B$ and $R_C$ are independently alkyl which may be further substituted with one or more substituents independently selected from oxo, hydroxy, halogen, amino, —NH(alkyl), —N(alkyl)(alkyl), cyano, nitro, haloalkyl, haloalkoxy, —O(alkyl), —NHC(O)(alkyl), —N(alkyl)C(O)(alkyl), —NHS(O)$_m$(alkyl), —S(O)$_m$(alkyl), —S(O)$_m$NH(alkyl), and —S(O)$_m$N(alkyl)(alkyl); where each m is 0, 1, or 2;

Y is independently selected at each occurrence from 5- to 8-membered carbocycles and heterocycles, which are saturated, partially unsaturated, or aromatic and contain zero, one or two hetero atoms selected from N, O, and S, and which may be further substituted with one or more substituents independently selected from the group consisting of halogen, oxo, hydroxy, amino, mono- or di($C_1$-$C_6$)alkylamino, nitro, cyano, $C_1$-$C_6$ alkyl, $C_1$-$C_6$ alkoxy, and —SO$_a$(alkyl); where a is 0, 1, or 2;

$R_1$ and $R_2$ are independently selected at each occurrence from hydrogen, halogen, hydroxy, alkyl, alkoxy, alkoxy, haloalkyl, haloalkoxy, nitro, cyano, amino, mono or di(alkyl)amino;

Ar is aryl, optionally substituted with 1, 2, or 3 substituents independently selected from the group consisting of oxo, haloalkyl, haloalkoxy, halogen, cyano, hydroxy, nitro, azido, alkanoyl, carboxamido, alkyl substituted with 0-2 $R_A$, alkyoxy substituted with 0-2 $R_A$, aryloxy, alkylthio alkylsulfinyl, alkylsulfonyl, amino, —NH(alkyl) where the alkyl is substituted with 0-2 $R_A$, —N(alkyl)(alkyl) where each alkyl is substituted with 0-2 $R_A$, aryl, arylalkyl, arylalkoxy, heteroaryl and heterocycloalkyl.

2. A compound or salt according to claim 1, wherein
R is hydroxy, alkyl, cycloalkyl, alkoxy, or cycloalkyloxy each of which is optionally substituted with oxo, haloalkyl, haloalkoxy halogen, cyano, hydroxy, alkyl, nitro, azido, alkanoyl, carboxamido, alkoxy, aryloxy, alkylthio, alkylsulfinyl, alkylsulfonyl, amino, mono or dialkylamino, aryl, arylalkyl, arylalkoxy, heteroaryl or heterocycloalkyl; or
R is phenyl optionally mono-, di-, or trisubstituted with substituents independently chosen from halogen, cyano, nitro, haloalkyl, haloalkoxy, hydroxy, amino, alkyl substituted with 0-2 $R_A$, alkoxy substituted with 0-2 $R_A$, —NH(alkyl) substituted with 0-2 $R_A$, —N(alkyl)(alkyl) where each alkyl is independently substituted with 0-2 $R_A$, phenyl substituted with 0-3 $R_A$, —$XR_B$, and $R_C$;
Ar is phenyl, optionally mono-, di-, or trisubstituted with substitutents independently chosen from oxo, halogen, cyano, nitro, haloalkyl, haloalkoxy, hydroxy, amino, alkyl substituted with 0-2 $R_A$, alkoxy substituted with 0-2 $R_A$, —NH(alkyl) substituted with 0-2 $R_A$, —N(alkyl)(alkyl) where each alkyl is independently substituted with 0-2 $R_A$, —$XR_B$, and $R_C$;

$R_A$ is independently selected at each occurrence from the group consisting of halogen, hydroxy, alkyl, alkoxy, —NH(alkyl), —N(alkyl)(alkyl), morpholinyl, pyrrolidinyl, piperidinyl, thiomorpholinyl, piperazinyl, —S(O)$_m$(alkyl), where m is 0, 1, or 2, haloalkyl, haloalkoxyoxy, —CO(alkyl), CONH(alkyl), CON(alkyl)(alkyl), —XR$_B$, and Y;

wherein each alkyl independently is a straight or branched chain group having 1 to 12 carbon atoms.

3. A compound or salt according to claim 1, wherein

R is hydroxy, $C_1$-$C_6$alkyl, cycloalkyl, $C_1$-$C_6$alkoxy, or cycloalkyloxy each of which is optionally substituted with oxo, $C_1$-$C_6$haloalkyl, $C_1$-$C_6$haloalkoxy halogen, cyano, hydroxy, $C_1$-$C_6$alkyl, nitro, azido, $C_1$-$C_6$alkanoyl, carboxamido, $C_1$-$C_6$alkoxy, aryloxy, $C_1$-$C_6$alkylthio, $C_1$-$C_6$alkylsulfinyl, $C_1$-$C_6$alkylsulfonyl, amino, mono or di($C_1$-$C_6$)alkylamino, aryl, aryl($C_1$-$C_4$)alkyl, aryl($C_1$-$C_4$)alkoxy, heteroaryl or heterocycloalkyl; or R is phenyl, optionally mono-, di-, or trisubstituted with substituents independently chosen from halogen, cyano, nitro, $C_1$-$C_6$haloalkyl, $C_1$-$C_6$haloalkoxy, hydroxy, amino, $C_1$-$C_6$alkyl substituted with 0-2 $R_A$, $C_1$-$C_6$alkoxy substituted with 0-2 $R_A$, —NH($C_1$-$C_6$alkyl) substituted with 0-2 $R_A$, —N($C_1$-$C_6$alkyl)($C_1$-$C_6$alkyl) where each alkyl is independently substituted with 0-2 $R_A$, phenyl substituted with 0-3 $R_A$, —XR$_B$, and $R_C$;

$R_1$ and $R_2$ are independently selected at each occurrence from hydrogen, halogen, hydroxy, $C_1$-$C_6$ alkyl, $C_1$-$C_6$ alkoxy, $C_1$-$C_6$haloalkyl, $C_1$-$C_6$haloalkoxy, nitro, cyano, amino, and mono- and di-($C_1$-$C_6$)alkylamino;

Ar is phenyl, optionally mono-, di-, or trisubstituted with substituents independently chosen from oxo, halogen, cyano, nitro, $C_1$-$C_6$haloalkyl, $C_1$-$C_6$haloalkoxy, hydroxy, amino, $C_1$-$C_6$alkyl substituted with 0-2 $R_A$, $C_1$-$C_6$alkoxy substituted with 0-2 $R_A$, —NH($C_1$-$C_6$alkyl) substituted with 0-2 $R_A$, —N($C_1$-$C_6$alkyl)($C_1$-$C_6$alkyl) where each $C_1$-$C_6$alkyl is independently substituted with 0-2 $R_A$, —XR$_B$, and $R_C$;

$R_A$ is independently selected at each occurrence from the group consisting of halogen, hydroxy, $C_1$-$C_6$alkyl, $C_1$-$C_6$alkoxy, —NH($C_1$-$C_6$alkyl), —N($C_1$-$C_6$alkyl)($C_1$-$C_6$alkyl), morpholinyl, pyrrolidinyl, piperidinyl, thiomorpholinyl, piperazinyl, —S(O)$_m$(alkyl), where m is 0, 1, or 2, $C_1$-$C_6$haloalkyl, $C_1$-$C_6$haloalkoxy, —CO($C_1$-$C_6$alkyl), CONH($C_1$-$C_6$alkyl), CON($C_1$-$C_6$alkyl)($C_1$-$C_6$alkyl), —XR$_B$, and Y; and $R_B$ and $R_C$ are independently $C_1$-$C_6$alkyl which may be further substituted with one or more substituents independently selected from oxo, hydroxy, halogen, amino, —NH($C_1$-$C_6$alkyl), —N($C_1$-$C_6$alkyl)($C_1$-$C_6$alkyl), cyano, nitro, $C_1$-$C_6$haloalkyl, $C_1$-$C_6$haloalkoxy, —O($C_1$-$C_6$alkyl), —NHC(O)($C_1$-$C_6$alkyl), —N($C_1$-$C_6$alkyl)C(O)($C_1$-$C_6$alkyl), —NHS(O)$_m$($C_1$-$C_6$alkyl) —S(O)$_m$($C_1$-$C_6$alkyl), —S(O)$_m$NH($C_1$-$C_6$alkyl) and —S(O)$_m$N($C_1$-$C_6$alkyl)($C_1$-$C_6$alkyl); where each m is 0, 1, or 2.

4. A compound or salt according to claim 1, wherein

Ar is phenyl, optionally substituted with up to three groups selected from halogen, cyano, nitro, $C_1$-$C_6$haloalkyl, $C_1$-$C_6$haloalkoxy, hydroxy, amino, and $C_1$-$C_6$alkyl substituted with 0-2 $R_A$, $C_1$-$C_6$alkoxy substituted with 0-2 $R_A$, —NH($C_1$-$C_6$alkyl) substituted with 0-2 $R_A$, and —N($C_1$-$C_6$alkyl)($C_1$-$C_6$alkyl) where each alkyl is independently substituted with 0-2 $R_A$, —XR$_B$, or $R_C$ $R_A$ is independently selected at each occurrence the group consisting of halogen, hydroxy, $C_1$-$C_6$alkyl, $C_1$-$C_6$alkoxy, —NH($C_1$-$C_6$alkyl), —N($C_1$-$C_6$alkyl)($C_1$-$C_6$alkyl), $C_1$-$C_6$haloalkyl, $C_1$-$C_6$haloalkoxy, —XR$_B$ and Y;

X is independently selected at each occurrence from the group consisting of —CH$_2$—, —CHR$_C$—, —O—, —NH—, —NR$_C$—, and —C(=O)—;

$R_B$ and $R_C$ are independently $C_1$-$C_6$ alkyl, $C_3$-$C_7$cycloalkyl, or $C_3$-$C_7$cycloalkyl($C_1$-$C_6$)alkyl, each of is optionally substituted with one or more substituents independently selected from oxo, hydroxy, halogen, amino, cyano, nitro, $C_1$-$C_6$ haloalkyl, $C_1$-$C_6$ haloalkoxy, $C_1$-$C_6$ alkyl, $C_1$-$C_6$ alkoxy, mono- or di($C_1$-$C_6$)alkylamino, —NHC(O)($C_{1-6}$ alkyl), and —N($C_1$-$C_6$ alkyl)C(O)($C_1$-$C_6$ alkyl), where m is 0, 1, or 2; and Y is morpholinyl, homopiperazinyl, piperazinyl, homo piperidinyl, piperidinyl, tetrahydropyridyl, imidazolyl, imidazolinyl, or imidazolidinyl.

5. A compound or salt according to claim 4, wherein

Ar is phenyl, optionally substituted with up to three groups selected from halogen, nitro, $C_1$-$C_6$haloalkyl, $C_1$-$C_6$haloalkoxy, hydroxy, amino, and $C_{1-6}$ alkyl substituted with 0-2 $R_A$, $C_{1-6}$ alkoxy substituted with 0-2 $R_A$, —NH($C_1$-$C_6$alkyl) substituted with 0-2 $R_A$, and —N($C_1$-$C_6$alkyl)($C_1$-$C_6$alkyl) where each alkyl is independently substituted with 0-2 $R_A$, —XR$_B$, or $R_C$ $R_A$ is independently selected at each occurrence from the group consisting of halogen, hydroxy, $C_1$-$C_6$alkyl, $C_1$-$C_6$alkoxy, —NH($C_1$-$C_4$alkyl), —N($C_1$-$C_3$alkyl)($C_1$-$C_3$alkyl), $C_1$-$C_3$haloalkyl, $C_1$-$C_3$haloalkoxy, —XR$_B$, and Y;

X is independently selected at each occurrence from the group consisting of —CH$_2$—, —CHR$_C$—, —O—, —NH—, —NR$_C$—, and —C(=O)—;

$R_B$ and $R_C$ are independently $C_1$-$C_6$alkyl or $C_3$-$C_7$ cycloalkyl, each of is optionally substituted with one or two substituents independently selected from hydroxy, halogen, amino, cyano, nitro, $C_1$-$C_6$haloalkyl, $C_1$-$C_6$haloalkoxy, $C_1$-$C_6$ alkyl, $C_1$-$C_6$alkoxy, and mono- or di($C_1$-$C_6$)alkylamino; and Y is morpholinyl, homopiperazinyl, piperazinyl, homo piperidinyl, piperidinyl, tetrahydropyridyl, imidazolyl, imidazolinyl, or imidazolidinyl.

6. A compound or salt according to claim 1, wherein Ar is phenyl, optionally mono-, di-, or tri-substituted with substituents independently chosen from halogen, $C_1$-$C_6$ alkyl, $C_1$-$C_6$ alkoxy, amino, mono- or di($C_1$-$C_6$)alkylamino, $C_1$-$C_6$alkoxy($C_1$-$C_6$)alkoxy, $C_1$-$C_6$alkylamino($C_1$-$C_6$)alkoxy, amino ($C_1$-$C_6$)alkoxy, di($C_1$-$C_6$)alkylamino($C_1$-$C_6$)alkoxy, $C_1$-$C_6$ alkoxy($C_1$-$C_6$)alkylamino, alkyl substituted with morpholinyl, homopiperazinyl, piperazinyl, homopiperidinyl, piperidinyl, tetrahydropyridyl, imidazolyl, imidazolinyl, imidazolidinyl, and $C_1$-$C_6$ alkoxy substituted with morpholinyl, homopiperazinyl, piperazinyl, homopiperidinyl, piperidinyl, tetrahydropyridyl, imidazolyl, imidazolinyl, or imidazolidinyl.

7. A compound or salt according to claim 1, wherein
Ar is phenyl, substituted with one of
i) halogen, $C_1$-$C_6$ alkyl, $C_1$-$C_6$ alkoxy, mono- or di-($C_1$-$C_6$)alkylamino, $C_1$-$C_6$alkoxy($C_1$-$C_6$)alkoxy, mono or di-($C_1$-$C_6$)alkylamino($C_1$-$C_6$)alkoxy, or
ii) $C_1$-$C_6$ alkoxy substituted with morpholinyl, homopiperazinyl, piperazinyl, homopiperidinyl, piperidinyl, tetrahydropyridyl, imidazolyl, imidazolinyl, or imidazolidinyl; and optionally further substituted with one or two substitutents independently chosen from: halogen, $C_1$-$C_4$ alkyl, $C_1$-$C_4$ alkoxy, amino, $C_1$-$C_6$ alkylamino, $C_1$-$C_3$ alkoxy($C_1$-$C_3$)alkoxy, $C_1$-$C_3$alkylamino($C_1$-$C_3$)alkoxy, amino($C_1$-$C_3$)alkoxy, $C_1$-$C_3$alkylamino($C_1$-$C_3$)alkoxy, and $C_1$-$C_6$ alkoxy($C_1$-$C_6$)alkylamino.

8. A compound or salt according to claim 7, wherein each $R_1$ and each $R_2$ is independently hydrogen, halogen, $C_1$-$C_6$ alkyl, $C_1C_6$ alkoxy, halo($C_1$-$C_6$)alkyl, halo($C_1$-$C_6$)alkoxy, cyano, amino, or amino ($C_1$-$C_6$) alkyl.

9. A compound or salt according to claim 8, wherein each $R_1$ and $R_2$ is independently selected from hydrogen, $C_1$-$C_2$ alkyl, $C_1$-$C_2$ alkoxy, cyano, amino, and halogen.

10. A compound or salt according to claim 9, wherein no more than three of $R_1$ and $R_2$ are other than hydrogen.

11. A compound or salt according to claim 10, wherein one, two, or three of $R_1$ and $R_2$ are independently chosen from hydrogen, halogen, methyl and ethyl, and the remaining $R_1$ and $R_2$ substituents are hydrogen.

12. A compound or salt according to claim 11, wherein
R is $C_1$-$C_6$alkyl, $C_1$-$C_6$alkoxy, phenyl($C_1$-$C_6$)alkyl, or phenyl, wherein the phenyl is unsubstituted or mono-, di-, or trisubstituted with halogen, cyano, nitro, halo($C_1$-$C_6$)alkyl, halo($C_1$-$C_6$)alkoxy, hydroxy, amino, $C_1$-$C_6$alkyl substituted with 0-2 $R_A$, $C_1$-$C_6$alkoxy substituted with 0-2 $R_A$, —NH($C_{1-6}$alkyl) substituted with 0-2 $R_A$, —N($C_1$-$C_6$alkyl)($C_1$-$C_6$alkyl) where each $C_1$-$C_6$alkyl is independently substituted with 0-2 $R_A$, phenyl substituted with 0-3 $R_A$, —$XR_B$, and $R_C$.

13. A compound according to claim 12, wherein
R is $C_1$-$C_6$ alkyl, $C_1$-$C_6$ alkoxy, or
phenyl($C_1$-$C_6$)alkyl, or phenyl where the aromatic portion of each is unsubstituted or mono-, di-, or trisubstituted with halogen, cyano, nitro, $C_1$-$C_6$haloalkyl, $C_1$-$C_6$haloalkoxy, hydroxy, amino, $C_1$-$C_6$ alkoxy, or $C_{1-6}$alkyl.

14. A compound, according to claim 1, wherein
Ar is phenyl, optionally substituted with up to three groups selected from halogen, cyano, nitro, $C_1$-$C_6$haloalkyl, $C_1$-$C_6$haloalkoxy, hydroxy, amino, and $C_1$-$C_6$alkyl substituted with 0-2 $R_A$, $C_1$-$C_6$alkoxy substituted with 0-2 $R_A$, —NH($C_1$-$C_6$alkyl) substituted with 0-2 $R_A$, —N($C_1$-$C_6$alkyl)($C_1$-$C_6$alkyl) where each alkyl is independently substituted with 0-2 $R_A$, —$XR_B$, or $R_C$;
$R_A$ is independently selected at each occurrence the group consisting of halogen, hydroxy, $C_1$-$C_6$alkyl, $C_1$-$C_6$alkoxy, —NH($C_1$-$C_6$alkyl), —N($C_1$-$C_6$alkyl)($C_1$-$C_6$alkyl), $C_1$-$C_6$haloalkyl, $C_1$-$C_6$haloalkoxy, CO($C_1$-$C_6$alkyl), CONH($C_1$-$C_6$alkyl), CON($C_1$-$C_6$alkyl)($C_1$-$C_6$alkyl), —$XR_B$ and Y;
X is independently selected at each occurrence from the group consisting of —$CH_2$—, —$CHR_C$—, —O—, —$S(O)_g$—, —NH—, —$NR_C$—, —C(=O)—, —C(=O)O—, —C(=O)NH—, —C(=O)$NR_C$—, —$S(O)_g$NH—, —$S(O)_g NR_C$—, NHC(=O)—, —$NR_C$C(=O)—, —$NHS(O)_g$—, and —$NR_C S(O)_g$—; where g is 0, 1, or 2;

$R_B$ and $R_C$ are independently alkyl groups which may be further substituted with one or more substituent(s) selected from oxo, hydroxy, halogen, amino, cyano, nitro, $C_1$-$C_6$haloalkyl, $C_1$-$C_6$haloalkoxy, —O($C_1$-$C_6$alkyl), —NH($C_{1-6}$ alkyl), —N($C_1$-$C_6$alkyl)($C_{1-6}$ alkyl), —NHC(O)($C_1$-$C_6$alkyl), —N(alkyl)C(O)($C_1$-$C_6$alkyl), —NHS(O)$_m$($C_1$-$C_6$alkyl), —S(O)$_m$($C_1$-$C_6$alkyl), —S(O)$_m$NH($C_1$-$C_6$alkyl), and —S(O)$_m$N($C_1$-$C_6$alkyl)($C_1$-$C_6$alkyl); where m is 0, 1, or 2; and
Y is morpholinyl, homopiperazinyl, piperazinyl, homo piperidinyl, piperidinyl, tetrahydropyridyl, imidazolyl, imidazolinyl, or imidazolidinyl, each of which is unsubstituted or substituted with one or more substituents independently chosen from halogen, oxo, hydroxy, amino, mono- or di($C_1$-$C_6$)alkylamino, nitro, cyano, $C_1$-$C_6$ alkyl, and $C_1$-$C_6$ alkoxy.

15. A compound or salt according to claim 4, wherein:
R is $C_1$-$C_4$alkyl, $C_1$-$C_4$alkoxy, or phenyl, where the phenyl is mono- or di-substituted with substituents independently chosen from halogen, cyano, nitro, $C_1$-$C_6$haloalkyl, $C_1$-$C_6$haloalkoxy, hydroxy, amino, $C_1$-$C_6$ alkoxy, $C_{1-6}$ alkyl, amino($C_1$-$C_6$)alkyl, mono- or di($C_1$-$C_6$)alkylamino($C_1$-$C_6$)alkyl, and mono- or di($C_1$-$C_6$)alkylamino($C_1$-$C_6$)alkoxy.

16. A compound or salt according to claim 7, wherein
Ar is phenyl,
substituted at the position para to the point of attachment of Ar with one of
i) halogen, $C_1$-$C_6$ alkyl, $C_1$-$C_6$ alkoxy, mono- or di-($C_1$-$C_6$)alkylamino, $C_1$-$C_6$alkoxy($C_1$-$C_6$) alkoxy, mono or di-($C_1$-$C_6$)alkylamino($C_1$-$C_6$) alkoxy, or
ii) $C_1$-$C_6$ alkoxy substituted with morpholinyl, homopiperazinyl, piperazinyl, homopiperidinyl, piperidinyl, tetrahydropyridyl, imidazolyl, imidazolinyl, or imidazolidinyl; and
optionally further substituted with one or two substituents independently chosen from halogen, $C_1$-$C_4$ alkyl, $C_1$-$C_4$ alkoxy, amino, $C_1$-$C_6$ alkylamino, $C_1$-$C_3$ alkoxy($C_1$-$C_3$)alkoxy, $C_1$-$C_3$ alkylamino($C_1$-$C_3$) alkoxy, amino($C_1$-$C_3$)alkoxy, $C_1$-$C_3$ alkylamino($C_1$-$C_3$)alkoxy, and $C_1$-$C_6$ alkoxy($C_1$-$C_6$)alkylamino;
R is $C_1$-$C_4$ alkoxy; and
one, two, or three of $R_1$ and $R_2$ are independently hydrogen, halogen, methyl or ethyl, and the remaining $R_1$ and $R_2$ substituents are hydrogen.

17. A compound or salt according to claim 7, wherein
Ar is phenyl
substituted at the position meta to the point of attachment of Ar with one of
i) halogen, $C_1$-$C_6$ alkyl, $C_1$-$C_6$ alkoxy, mono- or di-($C_1$-$C_6$)alkylamino, $C_1$-$C_6$alkoxy($C_1$-$C_6$) alkoxy, mono or di-($C_1$-$C_6$)alkylamino($C_1$-$C_6$) alkoxy, or
ii) $C_1$-$C_6$ alkoxy substituted with morpholinyl, homopiperazinyl, piperazinyl, homopiperidinyl, piperidinyl, tetrahydropyridyl, imidazolyl, imidazolinyl, or imidazolidinyl; and
optionally further substituted with one or two substituents independently chosen from halogen, $C_1$-$C_4$ alkyl, $C_1$-$C_4$ alkoxy, amino, $C_1$-$C_6$ alkylamino, $C_1$-$C_3$ alkoxy($C_1$-$C_3$)alkoxy, $C_1$-$C_3$ alkylamino($C_1$-$C_3$) alkoxy, amino($C_1$-$C_3$)alkoxy, $C_1$-$C_3$ alkylamino($C_1$-$C_3$)alkoxy, and $C_1$-$C_6$ alkoxy($C_1$-$C_6$)alkylamino;

R is $C_1$-$C_4$ alkoxy; and one, two, or three of $R_1$ and $R_2$ are independently hydrogen, halogen, methyl or ethyl, and the remaining $R_1$ and $R_2$ substituents are hydrogen.

18. A compound or salt according to claim 1, which is:
4-(4-Propyl-phenylimino)-4,5,6,7-tetrahydro-1H-indazole-3-carboxylic acid (4-propyl-phenyl)-amide,
4-Isopropylimino-4,5,6,7-tetrahydro-1H-indazole-3-carboxylic acid (3-fluoro-4-methoxy-phenyl)-amide;
4-Methoxyimino-4,5,6,7-tetrahydro-1H-indazole-3-carboxylic acid [4-(2-propylamino-ethoxy)-phenyl]-amide;
4-Methoxyimino-4,5,6,7-tetrahydro-1H-indazole-3-carboxylic acid (3-fluoro-4-methoxy-phenyl)-amide, or a pharmaceutically acceptable salt thereof.

19. A compound or salt according to claim 1, which is:
4-Ethoxyimino-4,5,6,7-tetrahydro-1H-indazole-3-carboxylic acid (3-fluoro-4-methoxy-phenyl)-amide,
4-Methoxyimino-4,5,6,7-tetrahydro-1H-indazole-3-carboxylic acid [4-(2-morpholin-4-yl-ethoxy)-3-fluorophenyl]-amide,
4-Ethoxyimino-4,5,6,7-tetrahydro-1H-indazole-3-carboxylic acid [4-(2-morpholin-4-yl-ethoxy)-3-fluorophenyl]-amide,
4-Methoxyimino-4,5,6,7-tetrahydro-1H-indazole-3-carboxylic acid [4-(2-propylamino-ethoxy)-3-fluoro-phenyl]-amide,
4-Ethoxyimino-4,5,6,7-tetrahydro-1H-indazole-3-carboxylic acid [4-(2-propylamino-ethoxy)-3-fluoro-phenyl]-amide,
4-Ethoxyimino-4,5,6,7-tetrahydro-1H-indazole-3-carboxylic acid [4-(2-dimethylamino-ethoxy)-phenyl]-amide, or a pharmaceutically acceptable salt thereof.

20. A pharmaceutical composition comprising a compound or salt according to claim 1 combined with at least one pharmaceutically acceptable carrier or excipient.

21. A method for the treatment of a disease or disorder associated with pathogenic agonism, inverse agonism or antagonism of the $GABA_A$ receptor, wherein the disease or disorder associated with pathogenic agonism, inverse agonism or antagonism of the $GABA_A$ receptor is anxiety, depression, sleep disorder, or cognitive impairment, said method comprising administering to a patient in need of such treatment an effective amount of a compound or salt of claim 1.

* * * * *